US012612452B2

(12) United States Patent
Hatsell et al.

(10) Patent No.: US 12,612,452 B2
(45) Date of Patent: Apr. 28, 2026

(54) HUMAN ANTIBODIES TO BONE MORPHOGENETIC PROTEIN 6

(71) Applicant: Regeneron Pharmaceuticals, Inc., Tarrytown, NY (US)

(72) Inventors: Sarah J. Hatsell, Piermont, NY (US); Vincent J. Idone, Ridgefield, CT (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 1144 days.

(21) Appl. No.: 17/617,657

(22) PCT Filed: Jun. 9, 2020

(86) PCT No.: PCT/US2020/036771
§ 371 (c)(1),
(2) Date: Dec. 9, 2021

(87) PCT Pub. No.: WO2020/251924
PCT Pub. Date: Dec. 17, 2020

(65) Prior Publication Data
US 2022/0251184 A1 Aug. 11, 2022

Related U.S. Application Data

(60) Provisional application No. 62/860,597, filed on Jun. 12, 2019.

(51) Int. Cl.
| | |
|---|---|
| *C07K 16/22* | (2006.01) |
| *A61K 9/00* | (2006.01) |
| *A61K 47/42* | (2017.01) |

(52) U.S. Cl.
CPC ............ *C07K 16/22* (2013.01); *A61K 9/0019* (2013.01); *A61K 47/42* (2013.01); *C07K 2317/21* (2013.01); *C07K 2317/92* (2013.01)

(58) Field of Classification Search
CPC .......................... C07K 16/22; C07K 2317/21; C07K 2317/92; C07K 2317/33; C07K 2317/76; A61K 9/0019; A61K 47/42; A61K 2039/505; A61P 7/06
See application file for complete search history.

(56) References Cited

U.S. PATENT DOCUMENTS

| | | | |
|---|---|---|---|
| 8,795,665 B2 | 8/2014 | Seo et al. | |
| 2014/0199314 A1 | 7/2014 | Lin et al. | |
| 2018/0171005 A1* | 6/2018 | Cong ..................... | C07K 16/22 |

FOREIGN PATENT DOCUMENTS

| | | |
|---|---|---|
| AU | 2016211890 A1 | 8/2016 |
| EP | 1360287 A1 | 11/2003 |
| JP | 2018-504893 A | 2/2018 |

| | | |
|---|---|---|
| WO | 2002/066630 A1 | 8/2002 |
| WO | 2016/098079 A2 | 6/2016 |
| WO | 2017/191437 A1 | 11/2017 |

OTHER PUBLICATIONS

Xia Y, Babitt JL, Sidis Y, Chung RT, Lin HY. Hemojuvelin regulates hepcidin expression via a selective subset of BMP ligands and receptors independently of neogenin. Blood. May 15, 2008;111(10):5195-204. (Year: 2008).*
Gershoni et al. Epitope mapping: the first step in developing epitope-based vaccines. BioDrugs. 2007;21(3):145-56. (Year: 2007).*
Blythe et al. Benchmarking B cell epitope prediction: underperformance of existing methods. Protein Sci. Jan. 2005;14(1):246-8. (Year: 2005).*
Schreiber et al. 3D-Epitope-Explorer (3DEX): localization of conformational epitopes within three-dimensional structures of proteins. J Comput Chem. Jul. 15, 2005;26(9):879-87. (Year: 2005).*
Ladner RC. Mapping the epitopes of antibodies. Biotechnol Genet Eng Rev. 2007;24:1-30. (Year: 2007).*
Almagro JC, Fransson J. Humanization of antibodies. Front Biosci. Jan. 1, 2008;13:1619-33. (Year: 2008).*
De Genst et al. Antibody repertoire development in camelids. Dev Comp Immunol. 2006;30(1-2):187-98. (Year: 2006).*
Ward ES, Güssow D, Griffiths AD, Jones PT, Winter G. Binding activities of a repertoire of single immunoglobulin variable domains secreted from Escherichia coli. Nature. Oct. 12, 1989;341(6242):544-6. (Year: 1989).*
Barthelemy et al. Comprehensive analysis of the factors contributing to the stability and solubility of autonomous human VH domains. J Biol Chem. Feb. 8, 2008;283(6):3639-3654. (Year: 2008).*
Choi et al. Predicting antibody complementarity determining region structures without classification. Mol. BioSyst., 2011,7, 3327-3334 (Year: 2011).*
Griffiths et al. Human anti-self antibodies with high specificity from phage display libraries. EMBO J. Feb. 1993;12(2):725-34 (Year: 1993).*
Klimka et al. Human anti-CD30 recombinant antibodies by guided phage antibody selection using cell panning. Br J Cancer 83, 252-260 (2000). (Year: 2000).*

(Continued)

*Primary Examiner* — Julie Wu
*Assistant Examiner* — Amber K Faust
(74) *Attorney, Agent, or Firm* — McCarter & English, LLP; Marcie B. Clarke

(57) ABSTRACT

The present invention provides antibodies that bind to BMP6, and methods of use. According to certain embodiments of the invention, the antibodies are fully human antibodies that bind to BMP6. The antibodies of the invention are useful for inhibiting binding of BMP6 to the hemojuvelin receptor, thereby down-regulating transcription and expression of hepcidin, thus providing a means of preventing or treating an iron-deficiency anemia or an iron-deficiency related disorder. In some embodiments, the antibodies of the present invention are used in treating at least one symptom or complication of an iron-deficiency anemia or an iron-deficiency related disorder.

14 Claims, 4 Drawing Sheets

Specification includes a Sequence Listing.

(56) References Cited

OTHER PUBLICATIONS

Beiboer et al. Guided selection of a pan carcinoma specific antibody reveals similar binding characteristics yet structural divergence between the original murine antibody and its human equivalent. J Mol Biol. Feb. 25, 2000;296(3):833-49. (Year: 2000).*

Dondelinger et al., Understanding the Significance and Implications of Antibody Numbering and Antigen-Binding Surface/Residue Definition. Front Immunol. Oct. 16, 2018;9:2278, 15 pages.

Germaschewski, Generation and development of KY1070, a fully human anti-BMP6 antibody for treatment of anemia of Chronic Disease. Programme of the 8th Congress of the International BioIron Society. https://www.embl.de/training/events/2019/BIR19-01/BIR19-01_Programme-V4.pdf.

Gershoni et al., Epitope mapping: the first step in developing epitope-based vaccines. BioDrugs. 2007;21(3):145-56.

Petzer et al., A fully human anti-BMP6 antibody reduces the need for erythropoietin in rodent models of the anemia of chronic disease. Blood. Aug. 27, 2020;136(9):1080-1090.

Rudikoff et al., Single amino acid substitution altering antigen-binding specificity. Proc Natl Acad Sci U S A. Mar. 1982;79(6):1979-83.

Stevens, Human Antibody Discovery, VelocImmune—A novel platform. Pharma Focus Asia, retrieved online at: https://www.pharmafocusasia.com/clinical-trials/human-antibody-discovery#:~:text=VelocImmune%20is%20a%20novel%20platform,additional%20engineering%20to%20drug%20characteristics. 4 pages, Jan. 1, 2008.

Zoller et al., Iron in Cancer, Infection, Kidney and Liver diseases: Innocent bystander or therapeutic target? https://bioironforum.org/wp-content/uploads/2018/10/7.-iron-in-cancer-infectio-kidney-and-liver-diseases.Theurl-zoller.pdf. 67 pages, (2018).

International Preliminary Report on Patentability for Application No. PCT/US2020/036771, dated Dec. 23, 2021, 15 pages.

International Search Report and Written Opinion for Application No. PCT/US2020/036771, dated Nov. 23, 2020, 23 pages.

Invitation to Pay Additional Fees for Application No. PCT/US2020/036771, dated Sep. 29, 2020, 18 pages.

* cited by examiner

Serum Hepcidin

HUMAN ANTIBODIES TO BONE MORPHOGENETIC PROTEIN 6

PRIORITY DATA

This application is a 35 U.S.C. § 371 national stage filing of International Application No. PCT/US2020/036771, filed on Jun. 9, 2020, which in turn claims priority to U.S. Provisional Application Ser. No. 62/860,597, filed Jun. 12, 2019, entitled "HUMAN ANTIBODIES TO BONE MORPHOGENETIC PROTEIN 6". The entire contents of each of the aforementioned applications are incorporated herein by reference.

REFERENCE TO A SEQUENCE LISTING

This application incorporates by reference the Sequence Listing submitted in computer readable form as file 0431_31 PCT_ST25, created on Jun. 5, 2019, and containing 43,200 bytes.

FIELD OF THE INVENTION

The present invention is related to human antibodies and antigen-binding fragments thereof that specifically bind to bone morphogenetic protein 6 (BMP6), and to therapeutic and diagnostic methods of using such antibodies and fragments.

BACKGROUND

BMP6 is a member of bone morphogenetic proteins, or BMPs, in the TGF-β superfamily. BMP6 has been shown to be involved in a variety of physiological process including in particular regulating iron levels.

The uptake of nutritional iron involves reduction of $Fe^{3+}$ in the intestinal lumen by ferric reductases and the subsequent transport of $Fe^{2+}$ across the apical membrane of enterocytes. The ferroportin-mediated efflux of $Fe^{2+}$ from enterocytes into the plasma is critical for systemic iron homoeostasis. This process is negatively regulated by hepcidin, a liver-derived peptide hormone that binds to ferroportin and promotes its phosphorylation, internalization and lysosomal degradation.

The expression of hepcidin is controlled transcriptionally. Iron-dependent induction of hepcidin requires BMP (bone morphogenetic protein) signaling. Iron triggers the expression of BMP6 in the liver sinusoidal endothelial cells, for binding to a BMP receptor on the surface of hepatocytes. BMP6 signaling leads to phosphorylation of SMAD1/5/8 and translocation along with SMAD4 to the nucleus, where it promotes hepcidin transcription upon binding to proximal and distal sites on its promoter.

Hemojuvelin (HJV, HFE2) is a co-receptor for BMP6 which enhances Bmp6 signaling in liver to induce Hepcidin expression. Mutations in hemojuvelin (HJV) have been found to lead to low hepcidin levels and excess iron accumulation (in the liver).

Antibodies which block BMP6 binding to hemojuvelin or its type II Bmp receptors provide a promising treatment for conditions associated with low plasma iron levels because reduction of such binding reduces plasma hepcidin levels which in turn promotes ferroportin-mediated efflux of $Fe^{2+}$ from enterocytes into the plasma.

SUMMARY OF THE INVENTION

The invention provides fully human monoclonal antibodies (mAbs) and antigen-binding fragments thereof that bind specifically to bone morphogenetic protein 6 (BMP6). Such antibodies may be useful to treat conditions associated with low plasma iron levels. The antibodies may act to reduce transcription of hepcidin, in turn promoting ferroportin-mediated efflux of $Fe^{2+}$ from enterocytes into the plasma. Such antibodies may prevent, halt the progression of, or lessen the severity of conditions associated with low plasma iron levels or ameliorate at least one symptom associated with such conditions, including but not limited to the group consisting of extreme fatigue, weakness, pale skin, chest pain, fast heartbeat, heart palpitations, shortness of breath, headache, dizziness, lightheadedness, cold hands, cold feet, inflammation of the tongue and restless legs. In some cases, the antibodies may be used to prevent or treat a condition or indication associated with low plasma iron levels such as iron-deficiency anemia or iron-deficiency related disorders. Such antibodies may be used alone or in conjunction with a second agent useful for treating iron-deficiency anemia or iron-deficiency related disorders. In certain embodiments, the antibodies specific for BMP6 may be given therapeutically in conjunction with a second agent to prevent, halt the progression of, or lessen the severity of conditions associated with low plasma iron levels or ameliorate at least one symptom associated with such conditions. In certain embodiments, the antibodies may be used prophylactically as stand-alone therapy to protect patients who are at risk for developing an iron-deficiency anemia or an iron-deficiency related disorder. For example, certain patient populations may be at risk for developing an iron-deficiency anemia or an iron-deficiency related disorder, including elderly patients or patients who have experienced a loss of blood. Any of such patient populations may benefit from treatment with the antibodies of the invention, when given alone or in conjunction with a second agent.

The antibodies of the present invention may be used to treat iron-deficiency anemia or an iron-deficiency related disorder in a patient. The antibodies can be full-length (for example, an IgG1 or IgG4 antibody) or may comprise only an antigen-binding portion (for example, a Fab, $F(ab')_2$ or scFv fragment), and may be modified to affect functionality, e.g., to eliminate residual effector functions (Reddy et al., (2000), J. Immunol. 164:1925-1933) or increase mAb half-life (Zalevsky et al., (2010), Nature Biotechnology 28:157-159). The present invention includes any antibody or antigen-binding fragment thereof which comprises any of the $V_H$ regions specified herein linked to a heavy chain constant region (e.g., human constant region) such as gamma (e.g., gamma-1, gamma-2, gamma-3 or gamma-4), delta, alpha, mu or epsilon and/or any $V_L$ region specified herein linked to a light chain constant region (e.g., human constant region) such as lambda or kappa.

Accordingly, in a first aspect, the invention provides an isolated fully human monoclonal antibody or antigen-binding fragment thereof that specifically binds to BMP6.

In one embodiment, the isolated human antibody or antigen-binding fragment thereof binds to BMP6 with a $K_D$ equal to or less than $10^{-7}$ M as measured by surface plasmon resonance.

In some embodiments, the isolated antibody or antigen-binding fragment thereof exhibits one or more properties selected from the group consisting of: (a) binds to human BMP6 at 37° C. with a binding dissociation equilibrium constant ($K_D$) of less than about 2 nM as measured by surface plasmon resonance; (b) binds to human BMP6 at 37° C. with a dissociative half-life (t %) of greater than about 130 minutes as measured by surface plasmon resonance; (c) binds to human BMP6 at 25° C. with a $K_D$ of less than about 1 nM as measured by surface plasmon resonance; (d) binds to human BMP6 at 25° C. with a t½, of greater than about 180 minutes as measured by surface plasmon resonance; (e) binds to a mouse BMP6 at 37° C. with a binding dissociation equilibrium constant ($K_D$) of less than about 10 nM as measured by surface plasmon resonance; (f) binds to a mouse BMP6 at 37° C. with a dissociative half-life (t½) of greater than about 70 minutes as measured by surface plasmon resonance; (g) binds to a mouse BMP6 at 25° C. with a $K_D$ of less than about 4 nM as measured by surface plasmon resonance; and (h) binds to a mouse BMP6 at 25° C. with a t½ of greater than about 80 minutes as measured by surface plasmon resonance.

In some cases, the isolated human antibody or antigen-binding fragment thereof which binds to BMP6 comprises three heavy chain complementarity determining regions (CDRs) (HCDR1, HCDR2 and HCDR3) contained within any one of the heavy chain variable region (HCVR) sequences selected from the group consisting of SEQ ID NOs: 1 and 3; and/or three light chain CDRs (LCDR1, LCDR2 and LCDR3) contained within any one of the light chain variable region (LCVR) sequences selected from the group consisting of SEQ ID NOs: 2 and 4. Methods and techniques for identifying CDRs within HCVR and LCVR amino acid sequences are well known in the art and can be used to identify CDRs within the specified heavy chain variable region(s) (HCVR) and/or light chain variable region(s) (LCVR) amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); AI-Lazikani et al., (1997), *J. Mol. Biol.* 273:927-948; and Martin et al., (1989), *Proc. Natl. Acad. Sci. USA* 86:9268-9272. Public databases are also available for identifying CDR sequences within an antibody.

In some embodiments, the isolated human antibody or antigen-binding fragment thereof, which binds to BMP6, comprises a HCVR having an amino acid sequence selected from the group consisting of SEQ ID NOs: 1 and 3.

In some embodiments, the isolated human antibody or antigen-binding fragment thereof, which binds to BMP6, comprises a LCVR having an amino acid sequence selected from the group consisting of SEQ ID NOs: 2 and 4.

In some cases, the isolated human antibody or antigen-binding fragment thereof, which binds to BMP6, comprises (a) a HCVR having an amino acid sequence selected from the group consisting of SEQ ID NOs: 1 and 3; and (b) a LCVR having an amino acid sequence selected from the group consisting of SEQ ID NOs: 2 and 4.

In one embodiment, the isolated human antibody or antigen-binding fragment thereof, which binds to BMP6, comprises:

(a) a HCDR1 domain having an amino acid sequence selected from the group consisting of SEQ ID NOs: 5 and 11;

(b) a HCDR2 domain having an amino acid sequence selected from the group consisting of SEQ ID NOs: 6 and 12;

(c) a HCDR3 domain having an amino acid sequence selected from the group consisting of SEQ ID NOs: 7 and 13;

(d) a LCDR1 domain having an amino acid sequence selected from the group consisting of SEQ ID NOs: 8 and 14;

(e) a LCDR2 domain having an amino acid sequence selected from the group consisting of SEQ ID NOs: 9 and 15; and (f) a LCDR3 domain having an amino acid sequence selected from the group consisting of SEQ ID NOs: 10 and 16.

In various embodiments, the invention provides a fully human monoclonal antibody or antigen-binding fragment thereof that binds to BMP6, wherein the antibody or fragment thereof exhibits one or more of the following characteristics: (i) comprises a HCVR having an amino acid sequence selected from the group consisting of SEQ ID NOs: 1 and 3, or a substantially similar sequence thereof having at least 90%, at least 95%, at least 98% or at least 99% sequence identity; (ii) comprises a LCVR having an amino acid sequence selected from the group consisting of SEQ ID NOs: 2 and 4, or a substantially similar sequence thereof having at least 90%, at least 95%, at least 98% or at least 99% sequence identity; (iii) comprises a HCDR1 domain having an amino acid sequence selected from the group consisting of SEQ ID NOs 5 and 11, or a substantially similar sequence thereof having at least 90%, at least 95%, at least 98% or at least 99% sequence identity; and a LCDR1 domain having an amino acid sequence selected from the group consisting of SEQ ID NOs: 8 and 14, or a substantially similar sequence thereof having at least 90%, at least 95%, at least 98% or at least 99% sequence identity; (iv) comprises a HCDR2 domain having an amino acid sequence selected from the group consisting of SEQ ID NOs: 6 and 12, or a substantially similar sequence thereof having at least 90%, at least 95%, at least 98% or at least 99% sequence identity; a HCDR3 domain having an amino acid sequence selected from the group consisting of SEQ ID NOs: 7 and 13, or a substantially similar sequence thereof having at least 90%, at least 95%, at least 98% or at least 99% sequence identity; a LCDR1 domain having an amino acid sequence selected from the group consisting of SEQ ID NOs: 8 and 14, or a substantially similar sequence thereof having at least 90%, at least 95%, at least 98% or at least 99% sequence identity; a LCDR2 domain having an amino acid sequence selected from the group consisting of SEQ ID NOs: 9 and 15, or a substantially similar sequence thereof having at least 90%, at least 95%, at least 98% or at least 99% sequence identity; and a LCDR3 domain having an amino acid sequence selected from the group consisting of SEQ ID NOs: 10 and 16, or a substantially similar sequence thereof having at least 90%, at least 95%, at least 98% or at least 99% sequence identity; and/or (v) binds to BMP6 with a $K_D$ equal to or less than $10^{-7}$ M as measured by surface plasmon resonance.

In another aspect, the invention provides an isolated antibody or antigen-binding fragment thereof that competes for binding to BMP6 with a reference antibody or antigen-binding fragment comprising the complementarity determining regions (CDRs) of a heavy chain variable region (HCVR) comprising the amino acid sequence selected from the group consisting of SEQ ID NOs: 1 and 3; and the CDRs of a light chain variable region (LCVR) comprising the amino acid sequence selected from the group consisting of SEQ ID NOs: 2 and 4.

In another aspect, the invention provides an isolated antibody or antigen-binding fragment thereof that binds the same epitope on BMP6 as a reference antibody or antigen-binding fragment comprising the CDRs of a heavy chain variable region (HCVR) comprising the amino acid sequence selected from the group consisting of SEQ ID NOs: 1 and 3; and the CDRs of a light chain variable region (LCVR) comprising the amino acid sequence selected from the group consisting of SEQ ID NOs: 2 and 4.

In some embodiments, the invention provides an isolated human antibody or antigen-binding fragment thereof that binds BMP6, wherein the antibody or fragment thereof comprises a HCVR/LCVR amino acid sequence pair selected from the group consisting of SEQ ID NOs: 1/3 and 2/4.

In another aspect, the invention provides nucleic acid molecules encoding anti-BMP6 antibodies or fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In some embodiments, the invention provides an antibody or fragment thereof comprising a HCVR encoded by a nucleic acid sequence selected from the group consisting of SEQ ID NOs: 17 and 19, or a substantially identical sequence having at least 90%, at least 95%, at least 98%, or at least 99% homology thereof.

In some embodiments, the antibody or fragment thereof further comprises a LCVR encoded by a nucleic acid sequence selected from the group consisting of SEQ ID NOs: 18 and 20, or a substantially identical sequence having at least 90%, at least 95%, at least 98%, or at least 99% homology thereof.

In some cases, the invention provides an antibody or antigen-binding fragment of an antibody comprising a HCDR3 domain encoded by a nucleotide sequence selected from the group consisting of SEQ ID NOs: 23 and 29, or a substantially similar sequence thereof having at least 90%, at least 95%, at least 98% or at least 99% sequence identity; and a LCDR3 domain encoded by a nucleotide sequence selected from the group consisting of SEQ ID NOs: 26 and 32, or a substantially similar sequence thereof having at least 90%, at least 95%, at least 98% or at least 99% sequence identity.

In some embodiments, the invention provides an antibody or fragment thereof further comprising a HCDR1 domain encoded by a nucleotide sequence selected from the group consisting of SEQ ID NOs: 21 and 27, or a substantially similar sequence thereof having at least 90%, at least 95%, at least 98% or at least 99% sequence identity; a HCDR2 domain encoded by a nucleotide sequence selected from the group consisting of SEQ ID NOs: 22 and 28, or a substantially similar sequence thereof having at least 90%, at least 95%, at least 98% or at least 99% sequence identity; a LCDR1 domain encoded by a nucleotide sequence selected from the group consisting of SEQ ID NOs: 24 and 30, or a substantially similar sequence thereof having at least 90%, at least 95%, at least 98% or at least 99% sequence identity; and a LCDR2 domain encoded by a nucleotide sequence selected from the group consisting of SEQ ID NOs: 25 and 31, or a substantially similar sequence thereof having at least 90%, at least 95%, at least 98% or at least 99% sequence identity.

In some embodiments, the antibody or antigen-binding fragment thereof that binds to BMP6, as described herein, may be linked to a detectable label such as a radionuclide label or an MRI-detectable label.

In another aspect, the invention provides a pharmaceutical composition comprising an isolated fully human monoclonal antibody or antigen-binding fragment thereof that binds to BMP6, as described above or herein, and a pharmaceutically acceptable carrier or diluent.

In some embodiments, the pharmaceutical composition comprises a fully human monoclonal antibody that binds to BMP6 having any one or more of the characteristics described above or herein. In one embodiment, the antibody binds to BMP6 with a $K_D$ equal to or less than $10^{-7}$M. In various embodiments, the composition comprises an antibody that binds to BMP6 and has a HCVR/LCVR amino acid sequence pair selected from the group consisting of SEQ ID NOs: 1/3 and 2/4. The present invention also provides an isolated human antibody or antigen-binding fragment, wherein the antibody or antigen-binding fragment comprises (i) a light chain immunoglobulin comprising the amino acid sequence set forth in SEQ ID NO: 34, and a heavy chain immunoglobulin comprising the amino acid sequence set forth in SEQ ID NO: 33; (ii) a light chain immunoglobulin comprising the amino acid sequence set forth in SEQ ID NO: 36, and a heavy chain immunoglobulin comprising the amino acid sequence set forth in SEQ ID NO: 35;

In some cases, the invention features a composition, which is a combination of an antibody or antigen-binding fragment of an antibody of the invention, and a second therapeutic agent. The second therapeutic agent may be a small molecule drug, a protein/polypeptide, an antibody, a nucleic acid molecule, such as an anti-sense oligonucleotide, or a siRNA. The second therapeutic agent may be synthetic or naturally derived. The second therapeutic agent may be any agent that is advantageously combined with the antibody or fragment thereof of the invention.

In certain embodiments, the second therapeutic agent may be an agent that helps to counteract or reduce any possible side effect(s) associated with the antibody or antigen-binding fragment of an antibody of the invention, if such side effect(s) should occur.

It will also be appreciated that the antibodies and pharmaceutically acceptable compositions of the present invention can be employed in combination therapies, that is, the antibodies and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an antibody may be administered concurrently with another agent used to treat the same disorder), or they may achieve different effects (e.g., control of any adverse effects). As used herein, additional therapeutic agents that are normally administered to treat or prevent a particular disease, or condition, are appropriate for the disease, or condition, being treated. When multiple therapeutics are co-administered, dosages may be adjusted accordingly, as is recognized in the pertinent art.

In another aspect, the invention provides a method for preventing, treating or managing an iron-deficiency anemia or an iron-deficiency related disorder. In certain embodiments, the invention provides a method for treating a patient suffering from an iron-deficiency anemia or an iron-deficiency related disorder, the method comprising administering to the patient an effective amount of an antibody or an antigen-binding fragment thereof that binds to BMP6; or a pharmaceutical composition comprising an effective amount of an antibody or an antigen-binding fragment thereof that binds to BMP6, such that the an iron-deficiency anemia or an iron-deficiency related disorder is either prevented, or lessened in severity and/or duration, or at least one symptom or complication associated with the condition or disease is prevented, or ameliorated, or that the frequency and/or duration of, or the severity of the iron-deficiency anemia or an iron-deficiency related disorder is reduced.

In some embodiments of the method, the pharmaceutical composition comprising the antibodies of the invention is administered to the patient in combination with a second therapeutic agent.

In embodiments of the invention, the antibody or antigen-binding fragment thereof or the pharmaceutical composition comprising the antibody is administered subcutaneously, intravenously, intradermally, orally or intramuscularly.

In related embodiments, the invention includes the use of an isolated anti-BMP6 antibody or antigen binding portion of an antibody of the invention in the manufacture of a medicament for the prevention or treatment of a disease or disorder related to or caused by an iron-deficiency anemia or an iron-deficiency related disorder. The invention also includes use of an isolated anti-BMP6 antibody or antigen binding portion thereof for preventing or treating a disease or disorder related to or caused by an iron-deficiency anemia or an iron-deficiency related disorder. In one embodiment, the invention includes the use of an isolated anti-BMP6 antibody or antigen-binding fragment thereof in the manufacture of a medicament for the treatment of an iron-deficiency anemia or an iron-deficiency related disorder. In some cases, the invention includes the use of an anti-BMP6 antibody or antigen-binding fragment thereof as discussed above or herein for treating a patient suffering from or at risk of developing an iron-deficiency anemia or an iron-deficiency related disorder.

Other embodiments will become apparent from a review of the ensuing detailed description.

DETAILED DESCRIPTION

Figure 1:
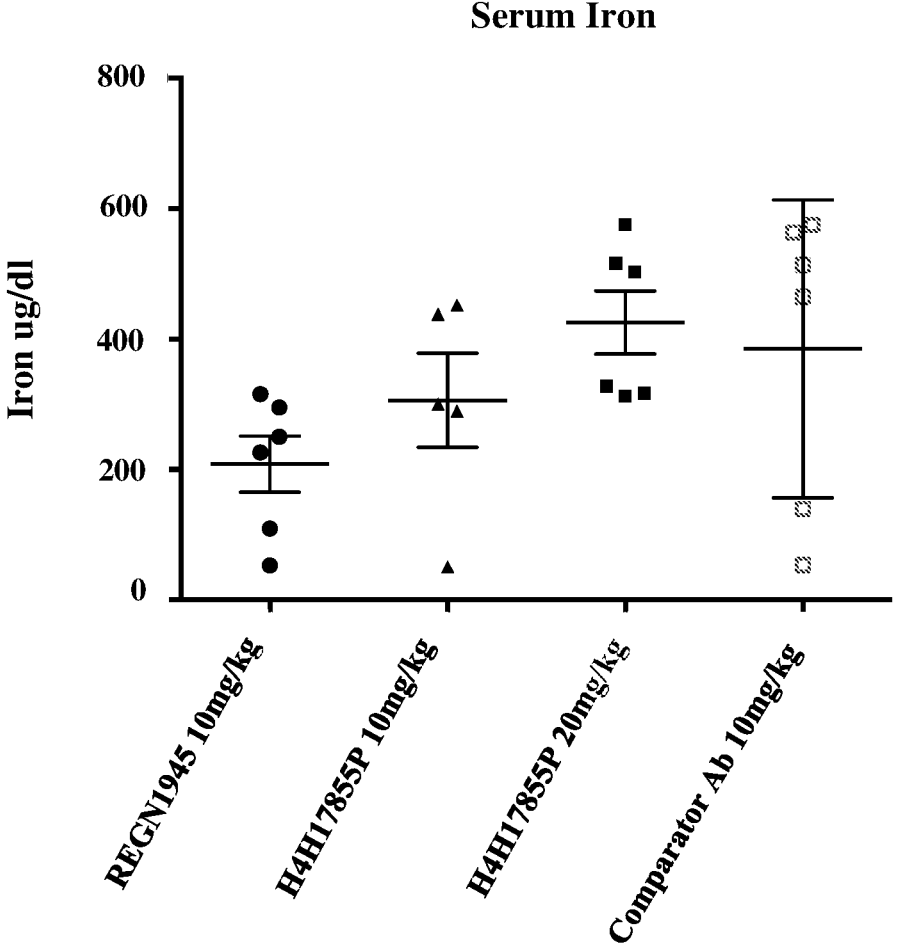
FIG. 1 shows mice receiving a BMP6 antibody of the invention, H4H17855P, had increased serum iron compared to mice receiving an isotype control antibody at 10 mg/kg. There is a dose dependent effect of the BMP6 antibody, which demonstrated increased serum iron at 20 mg/kg as compared to 10 mg/kg.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

Definitions

The terms "BMP6" and "Bone Morphogenetic Protein 6" refer, interchangeably, to a 57 kDa monomeric protein. BMP6 is a member of the transforming growth factor beta (TGF-beta) superfamily of regulatory molecules. The amino acid sequence of human BMP6 is shown in SEQ ID NO: 40. The amino acid sequence of mouse BMP6 is shown in SEQ ID NO: 42. Unless otherwise noted, reference to BMP6 refers to the human form.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (FASEB J. 1995, 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human BMP6 monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments that comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes fully human anti-BMP6 monoclonal antibodies comprising variants of any of the HCVR, LCVR, and/or CDR amino acid sequences disclosed herein having one or more conservative substitutions. For example, the present invention includes anti-BMP6 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1 \times 10^{-6}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies that bind specifically to BMP6 have been identified by surface plasmon resonance, e.g., BIACORE™. Moreover, multi-specific antibodies that bind to one domain in BMP6 and one or more additional antigens or a bi-specific that binds to two different regions of BMP6 are nonetheless considered antibodies that "specifically bind", as used herein.

The term "high affinity" antibody refers to those mAbs having a binding affinity to BMP6, expressed as $K_D$, of at least $10^{-7}$ M; preferably $10^{-8}$ M; more preferably $10^{-9}$ M, even more preferably $10^{-10}$ M, even more preferably $10^{-11}$ M, as measured by surface plasmon resonance, e.g., BIA-CORE™ or solution-affinity ELISA.

By the term "slow off rate", "Koff" or "kd" is meant to describe an antibody that dissociates from BMP6 with a rate constant of $1 \times 10^{-3}$ s$^{-1}$ or less, preferably $1 \times 10^{-4}$ s$^{-1}$ or less, as determined by surface plasmon resonance, e.g., BIA-CORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to BMP6.

In specific embodiments, antibody or antibody fragments of the invention may be conjugated to a therapeutic moiety ("immunoconjugate"), such as an antibiotic, a second anti-BMP6 antibody, or an antibody to a cytokine such as IL-1, IL-6, or TGF-β, or any other therapeutic moiety useful for treating an iron-deficiency anemia or an iron-deficiency related disorder.

An "isolated antibody", as used herein, is intended to refer to an antibody that is substantially free of other antibodies (Abs) having different antigenic specificities (e.g., an isolated antibody that specifically binds BMP6, or a fragment thereof, is substantially free of Abs that specifically bind antigens other than BMP6).

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen-binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25: 3389-3402, each of which is herein incorporated by reference.

In specific embodiments, the antibody or antibody fragment for use in the method of the invention may be mono-specific, bi-specific, or multi-specific. Multi-specific antibodies may be specific for different epitopes of one target polypeptide or may contain antigen-binding domains specific for epitopes of more than one target polypeptide.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

General Description

Bone morphogenetic protein 6 (BMP6) is a 57 kDa protein which has been shown to be involved in a variety of physiological processes including regulating iron levels. BMP6 signaling leads to phosphorylation of SMAD1/5/8 and translocation of SMAD4 to the nucleus, where it promotes hepcidin (a negative regulator of serum iron) transcription upon binding to proximal and distal sites on its promoter. Hemojuvelin (HJV, HFE2) is a co-receptor for BMP6 which, enhances signaling. Reduced binding of BMP6 to HJV reduces hepcidin transcription, thereby promoting serum iron levels.

The antibodies described herein demonstrate specific binding to BMP6 and in some embodiments, may be useful for treating patients suffering from iron-deficiency anemia or an iron-deficiency related disorder. They may be used alone or as adjunct therapy with other therapeutic moieties or modalities known in the art for treating iron-deficiency anemia or an iron-deficiency related disorder, such as, but not limited to, iron supplementation through iron supplements, dietary changes to promote serum iron and/or intravenous delivery of iron, blood transfusion, and iron promoting medications. They may be used in conjunction with additional antibodies specific for antigens other than BMP6 or may combined with other types of treatments.

In some embodiments, the antibodies described herein may be useful in preventing, treating or managing an iron-deficiency anemia or an iron-deficiency related disorder.

In certain embodiments, the antibodies of the invention are obtained from mice immunized with a primary immunogen, such as a native, full length human BMP6 (SEQ ID NO: 40) or BMP6 fragments, followed by immunization with a secondary immunogen, or with an immunogenically active fragment of BMP6.

The immunogen may be an immunogenic fragment of BMP6 or DNA encoding the fragment thereof. The immunogen may be BMP6 coupled to a histidine tag and/or to a fragment of Fc region of an antibody.

The amino acid sequence of full length human BMP6 is shown as SEQ ID NO: 40. The full length amino acid sequence of mouse BMP6 is shown as SEQ ID NO: 42.

In certain embodiments, antibodies that bind specifically to BMP6 may be prepared using fragments of the above-noted regions, or peptides that extend beyond the designated regions by about 5 to about 20 amino acid residues from either, or both, the N or C terminal ends of the regions described herein. In certain embodiments, any combination of the above-noted regions or fragments thereof may be used in the preparation of BMP6-specific antibodies. In certain embodiments, any one or more of the above-noted regions of BMP6, or fragments thereof may be used for preparing monospecific, bispecific, or multi-specific antibodies.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to BMP6. An antibody fragment may include a Fab fragment, a F(ab')$_2$ fragment, a Fv fragment, a dAb fragment, a fragment containing a CDR, or an isolated CDR. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CODR) such as a ODR3 peptide), or a constrained FR3-CDR3-FR4 peptide. Other engineered molecules, such as domain-specific antibodies, single-domain antibodies, domain-deleted antibodies, chimeric antibodies, CODR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (Xi) $V_L$-$C_H$1-$C_H$2; (xii) $V_L$-$C_H$1-$C_H$2-$C_H$3; (xiii) $V_L$-$C_H$2-$C_H$3; and (Xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

The present invention includes anti-BMP6 antibodies and antigen-binding fragments having immunoglobulin chains that include the amino acid sequences set forth herein as well as variants having cellular and/or in vitro post-translational modifications. For example, the present invention includes antibodies and antigen-binding fragments thereof that specifically bind to BMP6 comprising heavy and/or light chain amino acid sequences set forth herein (e.g., CDR-H1, CDR-H2, CDR-H3, CDR-L1, CDR-L2 and/or CDR-L3) as well as antibodies and fragments wherein one or more amino acid residues is glycosylated, one or more Asn residues is deamidated, one or more residues (e.g., Met, Trp and/or His) is oxidized, the N-terminal Gln is pyroglutamate (pyroE) and/or the C-terminal Lysine is missing.

The present invention includes recombinant methods for making anti-BMP6 antibodies or antigen-binding fragments thereof of the present invention, or an immunoglobulin chain thereof, comprising (i) introducing one or more polynucleotides encoding a light and/or a heavy immunoglobulin chain of said antibody or antigen-binding fragment (e.g., a heavy chain or $V_H$ thereof or immunoglobulin comprising the HCDR1, HCDR2 and HCDR3 thereof and/or a light chain or $V_L$ thereof or immunoglobulin comprising the LCDR1, LCDR2 and LCDR3 thereof), for example, wherein the polynucleotide is in a vector and/or is operably linked to a promoter; (ii) culturing the host cell (e.g., Chinese hamster ovary (CHO) cell or *Pichia* cell or *Pichia pastoris* cell) under condition favorable to expression of the polynucleotide(s) and, (iii) optionally, isolating the antibody or fragment or chain from the host cell and/or medium in which the host cell is grown. When making an antibody or antigen-binding fragment comprising more than one immunoglobulin chain, e.g., an antibody that comprises two heavy immunoglobulin chains and two light immunoglobulin chains, co-expression of the chains in a single host cell leads to association of the chains, e.g., in the cell or on the cell surface or outside the cell if such chains are secreted, so as to form the antibody or antigen-binding fragment molecule. The methods include those wherein only a heavy immunoglobulin chain or only a light immunoglobulin chain (e.g., any of those discussed herein including mature fragments and/or variable domains thereof) is expressed. Such chains are useful, for example, as intermediates in the expression of an antibody or antigen-binding fragment that includes such a chain. The present invention includes the products of such expression methods (e.g., antibodies, antigen-binding fragments, $V_H$s, or $V_L$s).

Preparation of Human Antibodies

Methods for generating human antibodies in transgenic mice are known in the art. Any such known methods can be used in the context of the present invention to make human antibodies that specifically bind to BMP6.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to BMP6 are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high-affinity chimeric antibodies are isolated having a human variable region and a mouse constant region. The antibodies are characterized and selected for desirable characteristics, including affinity, selectivity, epitope, etc. The mouse constant regions are replaced with a desired human constant region to generate the fully human antibody of the invention, for example wild type or modified IgG1 or IgG4. While the constant region selected may vary according to specific use, high affinity antigen-binding and target specificity characteristics reside in the variable region.

In general, the antibodies of the instant invention possess very high affinities, typically possessing $K_D$ of from about $10^{-12}$ through about $10^{-7}$ M, when measured by binding to antigen either immobilized on solid phase or in solution phase. The mouse constant regions are replaced with desired human constant regions to generate the fully human antibodies of the invention. While the constant region selected may vary according to specific use, high affinity antigen-binding and target specificity characteristics reside in the variable region.

Bioequivalents

The anti-BMP6 antibodies and antibody fragments of the present invention encompass proteins having amino acid sequences that vary from those of the described antibodies, but that retain the ability to bind BMP6. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present invention encompass sequences that comprise one or more additions, deletions, or substitutions of nucleotides when compared to the disclosed sequence, but that encode an antibody or antibody fragment that is essentially bioequivalent to an antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Anti-BMP6 Antibodies Comprising Fc Variants

According to certain embodiments of the present invention, anti-BMP6 antibodies are provided comprising an Fc domain comprising one or more mutations which enhance or diminish antibody binding to the FcRn receptor, e.g., at acidic pH as compared to neutral pH. For example, the present invention includes anti-BMP6 antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 2500 and 428L modification (e.g., T250Q and M428L); and a 307 and/or 308 modification(s) (e.g., 308F and/or 308P). In yet another embodiment, the modification comprises a 265A (e.g., D265A) and/or a 297A (e.g., N297A) modification.

For example, the present invention includes anti-BMP6 antibodies comprising an Fc domain comprising one or more pairs or groups of mutations selected from the group consisting of: 2500 and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). All possible combinations of the foregoing Fc domain mutations, and other mutations within the antibody variable domains disclosed herein, are contemplated within the scope of the present invention.

The present invention also includes anti-BMP6 antibodies comprising a chimeric heavy chain constant ($C_H$) region, wherein the chimeric $C_H$ region comprises segments derived from the $C_H$ regions of more than one immunoglobulin isotype. For example, the antibodies of the invention may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Provisional Appl. No. 61/759,578, filed Feb. 1, 2013, the disclosure of which is hereby incorporated by reference in its entirety).

Biological Characteristics of the Antibodies

In general, the antibodies of the present invention may function by binding to BMP6. In some embodiments, the antibodies of the present invention may bind to another antigen (cross-reactive antibodies).

In certain embodiments, the antibodies of the present invention may be bi-specific antibodies. The bi-specific antibodies of the invention may bind one epitope in one domain and may also bind one epitope in a second domain of BMP6. In certain embodiments, the bi-specific antibodies of the invention may bind two different epitopes in the same domain.

In one embodiment, the invention provides a fully human monoclonal antibody or antigen-binding fragment thereof that binds to BMP6, wherein the antibody or fragment thereof exhibits one or more of the following characteristics: (i) comprises a HCVR having an amino acid sequence selected from the group consisting of SEQ ID NO: 1 and 3, or a substantially similar sequence thereof having at least 90%, at least 95%, at least 98% or at least 99% sequence identity; (ii) comprises a LCVR having an amino acid sequence selected from the group consisting of SEQ ID NO: 2 and 4, or a substantially similar sequence thereof having at least 90%, at least 95%, at least 98% or at least 99% sequence identity; (iii) comprises a HCDR3 domain having an amino acid sequence selected from the group consisting of SEQ ID NO: 7 and 13, or a substantially similar sequence thereof having at least 90%, at least 95%, at least 98% or at least 99% sequence identity; and a LCDR3 domain having an amino acid sequence selected from the group consisting of SEQ ID NO: 10 and 16, or a substantially similar sequence thereof having at least 90%, at least 95%, at least 98% or at least 99% sequence identity; (iv) comprises a HCDR1 domain having an amino acid sequence selected from the group consisting of SEQ ID NO: 5 and 11, or a substantially similar sequence thereof having at least 90%, at least 95%, at least 98% or at least 99% sequence identity; a HCDR2 domain having an amino acid sequence selected from the group consisting of SEQ ID NO: 6 and 12, or a substantially similar sequence thereof having at least 90%, at least 95%, at least 98% or at least 99% sequence identity; a LCDR1 domain having an amino acid sequence selected from the group consisting of SEQ ID NO: 8 and 14, or a substantially similar sequence thereof having at least 90%, at least 95%, at least 98% or at least 99% sequence identity; and a LCDR2 domain having an amino acid sequence selected from the group consisting of SEQ ID NO: 9 and 15, or a substantially similar sequence thereof having at least 90%, at least 95%, at least 98% or at least 99% sequence identity; and (v) binds to BMP6 with a $K_D$ equal to or less than $10^{-7}$.

Certain anti-BMP6 antibodies of the present invention are able to bind to and neutralize the activity of BMP6, as determined by in vitro or in vivo assays. The ability of the antibodies of the invention to bind to and neutralize the activity of BMP6 may be measured using any standard method known to those skilled in the art, including binding assays, or activity assays, as described herein.

The peptides may be modified to include addition or substitution of certain residues for tagging or for purposes of conjugation to carrier molecules, such as, KLH. For example, a cysteine may be added at either the N-terminal or C-terminal end of a peptide, or a linker sequence may be added to prepare the peptide for conjugation to, for example, KLH for immunization.

The antibodies specific for BMP6 may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In one embodiment, the label may be a radionuclide, a fluorescent dye or a MRI-detectable label. In certain embodiments, such labeled antibodies may be used in diagnostic assays including imaging assays.

Epitope Mapping and Related Technologies

The present invention includes anti-BMP6 antibodies which interact with one or more amino acids found within one or more regions of BMP6. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within any of the aforementioned regions of the BMP6 molecule (e.g. a linear epitope in a domain). Alternatively, the epitope may consist of a plurality of non-contiguous amino acids (or amino acid sequences) located within either or both of the aforementioned regions of the BMP6 molecule (e.g. a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in *Antibodies*, Harlow and Lane (Cold Spring Harbor Press, Cold Spring Harbor, NY). Other methods include alanine scanning mutational analysis, peptide blot analysis (Reineke (2004) Methods Mol Biol 248:443-63), peptide cleavage analysis, crystallographic studies and NMR analysis. In addition, methods such as epitope excision, epitope extraction and chemical modification of antigens can be employed (Tomer (2000) Protein Science 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the peptides containing the deuterium-labeled residues that contain specific amino acids with which the antibody interacts. See, e.g., Ehring (1999) *Analytical Biochemistry* 267(2):252-259; Engen and Smith (2001) *Anal. Chem.* 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the invention into groups of antibodies binding different epitopes.

In certain embodiments, the anti-BMP6 antibodies or antigen-binding fragments thereof bind an epitope within any one or more of the regions exemplified in human BMP6, as exemplified in SEQ ID NO: 40, or to a fragment thereof.

The present invention includes human anti-BMP6 antibodies that bind to the same epitope, or a portion of the epitope, as any of the specific exemplary antibodies described herein, or an antibody having the CDR sequences of any of the exemplary antibodies described herein. Likewise, the present invention also includes anti-BMP6 antibodies that compete for binding to BMP6 or a BMP6 fragment with any of the specific exemplary antibodies described herein, or an antibody having the CDR sequences of any of the exemplary antibodies described herein.

One can easily determine whether an antibody binds to the same epitope as, or competes for binding with, a reference anti-BMP6 antibody by using routine methods known in the art. For example, to determine if a test antibody binds to the same epitope as a reference anti-BMP6 antibody of the invention, the reference antibody is allowed to bind to a BMP6 protein or peptide under saturating conditions. Next, the ability of a test antibody to bind to the BMP6 molecule is assessed. If the test antibody is able to bind to BMP6 following saturation binding with the reference anti-BMP6 antibody, it can be concluded that the test antibody binds to a different epitope than the reference anti-BMP6 antibody. On the other hand, if the test antibody is not able to bind to the BMP6 protein following saturation binding with the reference anti-BMP6 antibody, then the test antibody may bind to the same epitope as the epitope bound by the reference anti-BMP6 antibody of the invention.

To determine if an antibody competes for binding with a reference anti-BMP6 antibody, the above-described binding methodology is performed in two orientations: In a first orientation, the reference antibody is allowed to bind to a BMP6 protein under saturating conditions followed by assessment of binding of the test antibody to the BMP6 molecule. In a second orientation, the test antibody is allowed to bind to a BMP6 molecule under saturating conditions followed by assessment of binding of the reference antibody to the BMP6 molecule. If, in both orientations, only the first (saturating) antibody is capable of binding to the BMP6 molecule, then it is concluded that the test antibody and the reference antibody compete for binding to BMP6. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The invention encompasses a human anti-BMP6 monoclonal antibody conjugated to a therapeutic moiety ("immunoconjugate"), such as an agent that is capable of reducing the severity of an iron-deficiency anemia or an iron-deficiency related disorder, or to ameliorate at least one symptom associated with an iron-deficiency anemia or an iron-deficiency related disorder. As used herein, the term "immunoconjugate" refers to an antibody that is chemically or biologically linked to a radioactive agent, a cytokine, an interferon, a target or reporter moiety, an enzyme, a toxin, or a therapeutic agent. The antibody may be linked to the radioactive agent, cytokine, interferon, target or reporter moiety, enzyme, toxin, or therapeutic agent at any location along the molecule so long as it is able to bind its target. An example of immunoconjugate is an antibody drug conjugate. In some embodiments, the agent may be a second different antibody to BMP6, or to a cytokine such as IL-1, IL-6, or a chemokine such as TGF-β. The type of therapeutic moiety that may be conjugated to the anti-BMP6 antibody will take into account the condition to be treated and the desired therapeutic effect to be achieved. Examples of suitable agents for forming immunoconjugates are known in the art; see for example, WO 05/103081. The preparation of immunoconjugates and immunotoxins is generally well known in the art (see, e.g., U.S. Pat. No. 4,340,535). Immunoconjugates are described in detail, for example, in U.S. Pat. Nos. 7,250,492, 7,420,040 and 7,411,046, each of which is incorporated herein in their entirety.

Multi-Specific Antibodies

The antibodies of the present invention may be monospecific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multi-specific antibody with a second binding specificity. For example, the present invention includes bi-specific antibodies wherein one arm of an immunoglobulin is specific for the N-terminal region of BMP6, or a fragment thereof, and the other arm of the immunoglobulin is specific for the C-terminal region of BMP6, or a second therapeutic target, or is conjugated to a therapeutic moiety. An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to BMP6 as compared to a bi-specific antibody lacking the amino acid difference. In one embodiment, the first Ig $C_H3$ domain binds BMP6 and the second Ig $C_H3$ domain contains a mutation that reduces or abolishes BMP6 binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Administration and Formulations

The invention provides therapeutic compositions comprising the anti-BMP6 antibodies or antigen-binding fragments thereof as discussed herein. The therapeutic compositions in accordance with the invention can be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, PA These formulations include, for example, powders, pastes, ointments, jellies, waxes, oils, lipids, lipid (cationic or anionic) containing vesicles (such as LIPOFECTIN®), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When the antibody of the present invention is used for preventing or treating an iron-deficiency anemia or an iron-deficiency related disorder, it is advantageous to intravenously administer the antibody of the present invention normally at a single dose of about 0.1 to about 100 mg/kg body weight, more preferably about 5 to about 100, about 10 to about 90, or about 20 to about 70 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) Science 249: 1527-1533).

The use of nanoparticles to deliver the antibodies of the present invention is also contemplated herein. Antibody-conjugated nanoparticles may be used both for therapeutic and diagnostic applications. Antibody-conjugated nanoparticles and methods of preparation and use are described in detail by Arruebo, M., et al. 2009 ("Antibody-conjugated nanoparticles for biomedical applications" in J. Nanomat. Volume 2009, Article ID 439389, 24 pages, doi: 10.1155/2009/439389), incorporated herein by reference. Nanoparticles for drug delivery have also been described in, for example, U.S. Pat. Nos. 8,277,812, 8,258,256, 8,257,740, 8,246,995, 8,236,330, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN® (Owen Mumford, Inc., Woodstock, UK), DISETRONIC™ pen (Disetronic Medical Systems, Burghdorf, Switzerland), HUMALOG MIX 75/25™ pen, HUMALOG® pen, HUMALIN 70/30™ pen (Eli Lilly and Co., Indianapolis, IN), NOVOPEN® I, II and III (Novo Nordisk, Copenhagen, Denmark), NOVOPEN JUNIOR™ (Novo Nordisk, Copenhagen, Denmark), BD pen (Becton Dickinson, Franklin Lakes, NJ), OPTIPEN®, OPTIPEN® PRO, OPTIPEN® STARLET, and OPTICLIK™ (Sanofi-aventis, Frankfurt, Germany), to name only a few. Examples of disposable pen delivery devices having applications in subcutaneous delivery of a pharmaceutical composition of the present invention include, but certainly are not limited to the SOLOSTAR® pen (Sanofi-aventis), the FLEXPEN® (Novo Nordisk), and the KWIKPEN® (HUMALOG®), the SURECLICK® Autoinjector (, the PENLET (Haselmeier, Stuttgart, Germany), the EPIPEN® (Mylan® and the HUMIRA® Pen (Abbott Labs, Abbott Park, IL), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms. The present invention includes an injection device (e.g., a pre-filled syringe or pre-filled auto-injector) or a vial (e.g., a glass or plastic vial) comprising an antibody or antigen-binding fragment of the present invention or pharmaceutical composition thereof which includes a pharmaceutically acceptable carrier.

Therapeutic Uses of the Antibodies

In certain embodiments of the invention, the present antibodies are useful for treating an iron-deficiency anemia or an iron-deficiency related disorder, or at least one symptom associated with an iron-deficiency anemia or an iron-deficiency related disorder. The antibodies of the invention are also contemplated for prophylactic use in patients at risk for developing an iron-deficiency anemia or an iron-deficiency related disorder. These patients include the elderly, or patients immunocompromised due to illness or treatment with immunosuppressive therapeutics. It is contemplated that the antibodies of the invention may be used alone, or in conjunction with a second agent, or third agent for treating an iron-deficiency anemia or an iron-deficiency related disorder, or for alleviating at least one symptom or complication associated with an iron-deficiency anemia or an iron-deficiency related disorder. The second or third agents may be delivered concurrently with the antibodies of the invention, or they may be administered separately, either before or after the antibodies of the invention. A patient that may receive an antibody or antigen-binding fragment of the invention or a pharmaceutical composition thereof includes, for example, an animal such as a mammal such as a human (e.g., an elderly human, for example, 65 years of age or older), rabbit, mouse, rat, cow, pig, dog, primate, horse or sheep.

In a further embodiment of the invention the present antibodies are used for the preparation of a pharmaceutical composition for treating patients suffering from an iron-deficiency anemia or an iron-deficiency related disorder.

Combination Therapies

Combination therapies may include an anti-BMP6 antibody of the invention and any additional therapeutic agent(s) that may be advantageously combined with an antibody of the invention, or with a biologically active fragment of an antibody of the invention.

The antibodies may be used in conjunction with other therapies, such as moieties or modalities known in the art for treating iron-deficiency anemia or an iron-deficiency related disorder, such as, but not limited to, iron supplementation through iron supplements, dietary changes to promote serum iron and/or intravenous delivery of iron, blood transfusion, and iron promoting medications.

The additional therapeutically active component(s) may be administered prior to, concurrent with, or after the administration of the anti-BMP6 antibody of the present invention. For purposes of the present disclosure, such administration regimens are considered the administration of an anti-BMP6 antibody "in combination with" one or more additional therapeutically active component(s).

Diagnostic Uses of the Antibodies

The anti-BMP6 antibodies of the present invention may also be used to detect and/or measure BMP6 in a sample, e.g., for diagnostic purposes. Exemplary diagnostic assays for BMP6 may comprise, e.g., contacting a sample, obtained from a patient, with an anti-BMP6 antibody of the invention, wherein the anti-BMP6 antibody is labeled with a detectable label or reporter molecule or used as a capture ligand to selectively isolate BMP6 from patient samples. Alternatively, an unlabeled anti-BMP6 antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure BMP6 in a sample include enzyme-linked immunosorbent assay (ELISA), radioimmunoassay (RIA), and fluorescence-activated cell sorting (FACS).

Samples that can be used in BMP6 diagnostic assays according to the present invention include any tissue or fluid sample obtainable from a patient, which contains detectable quantities of either BMP6, or fragments thereof, under normal or pathological conditions. Generally, levels of BMP6 in a particular sample obtained from a healthy patient (e.g., a patient not afflicted with an iron-deficiency anemia or an iron-deficiency related disorder) will be measured to initially establish a baseline, or standard, level of BMP6. This baseline level of BMP6 can then be compared against the levels of BMP6 measured in samples obtained from individuals suspected of having an iron-deficiency anemia or an iron-deficiency related disorder related condition, or symptoms associated with such condition.

The antibodies specific for BMP6 may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In some embodiments, the label may be detectable label such as a radionuclide, a fluorescent dye or a MRI-detectable label. Detectable labels may be linked to the antibodies wherein such antibodies may be used in imaging assays.

EXAMPLES

The following examples are put forth so as to provide those of ordinary skill in the art with a complete disclosure and description of how to make and use the methods and compositions of the invention, and are not intended to limit the scope of what the inventors regard as their invention. Unless indicated otherwise, parts are parts by weight, molecular weight is average molecular weight, temperature is in degrees Celsius, and pressure is at or near atmospheric.

Example 1. Generation of Human Antibodies to BMP6

Human antibodies to BMP6 were generated in a VELOCIMMUNE® mouse comprising DNA encoding human Immunoglobulin heavy and kappa light chain variable regions. The mice were immunized with a stabilized full-length BMP6 protein.

The antibody immune response was monitored by a BMP6-specific immunoassay. When a desired immune response was achieved, splenocytes were harvested and fused with mouse myeloma cells to preserve their viability and form hybridoma cell lines. The hybridoma cell lines were screened and selected to identify cell lines that produce BMP6-specific antibodies. The cell lines were used to obtain several anti-BMP6 chimeric antibodies (i.e., antibodies possessing human variable domains and mouse constant domains).

Exemplary antibodies generated as disclosed above were designated as H4H17855P and H4H17871P. The biological properties of the exemplary antibodies generated in accordance with the methods of this Example are further described in the Examples below.

Example 2. Heavy and Light Chain Variable Region Amino Acid Sequences

Table 1 sets forth the heavy and light chain variable region amino acid sequence pairs of selected antibodies specific for BMP6 and their corresponding antibody identifiers. Antibodies are typically referred to herein according to the following nomenclature: Fc prefix (e.g. "H4H"), followed by a numerical identifier (e.g., "7855" as shown in Table 1), followed by a "P" suffix. Thus, according to this nomenclature, an antibody may be referred to as, e.g., "H4H17855P". The H4H prefix on the antibody designations used herein indicates the particular Fc region of the antibody. For example, an "H4H" antibody has a human IgG4 Fc.

Example 3. Binding Kinetics of Human Monoclonal Antibodies to BMP6

Equilibrium dissociation constants ($K_D$ values) for human and mouse BMP6 binding to purified anti-BMP6 monoclonal antibodies of this invention were determined using a real-time surface plasmon resonance (SPR) biosensor instrument, MASS-1. All binding studies were performed in 10 mM HEPES, 150 mM NaCl, 3 mM EDTA, 1 µg/mL Heparin, and 0.05% v/v Surfactant Tween-20, pH 7.4 (HBS-EHT) running buffer at 25° C. and 37° C. The HCA sensor surface was first derivatized by amine coupling the monoclonal mouse anti-human Fc antibody (GE, #BR100839) and anti-BMP6 monoclonal antibodies were individually captured. Different concentrations of human BMP6 reagents (hBMP6; R&D Systems, Cat #507-BP; 60 nM-0.94 nM; 4-fold serial dilution) or mouse BMP6 (mBMP6; R&D Systems, Cat #6325-BM; 60 nM and 15 nM) prepared in HBS-EHT running buffer were injected over the captured anti-BMP6 monoclonal antibody for 4 minutes at a flow rate of 30 µL/minute, while the dissociation of BMP6 reagent bound to captured anti-BMP6 monoclonal antibody was monitored for 10 minutes in HBS-EHT running buffer. Kinetic association ($k_a$) and dissociation ($k_d$) rate constants were determined by fitting the real-time binding sensorgrams to a 1:1 binding model with mass transport limitation using Scrubber 2.0c software. Binding dissociation equilibrium constant ($K_D$) and dissociative half-life (t½) for different anti-BMP6 monoclonal antibodies were calculated from the kinetic rate constants as:

$$K_D(M) = \frac{kd}{ka}, \text{ and } t1/2 \text{ (min)} = \frac{\ln(2)}{60*kd}$$

Binding kinetic parameters for hBMP6 or mBMP6 binding to different anti-BMP6 monoclonal antibodies of this invention at 25° C. and 37° C. are shown in Tables 2 through 5.

As shown in Table 2, at 25° C., both antibodies of the invention bound human BMP6 with $K_D$ values of 195 pM and 355 pM. As shown in Table 3, at 37° C., both antibodies of the invention bound human BMP6 with $K_D$ values of 240 pM and 1.34 nM. As shown in Table 4, at 25° C., both antibodies of the invention bound mouse BMP6 with $K_D$ values of 3.39 nM and 3.55 nM. As shown in Table 5, at 37° C., both antibodies of the invention bound mouse BMP6 with $K_D$ values of 4.0 nM and 6.46 nM.

TABLE 1

| Antibody | SEQ ID NOs: | | | | | | | |
|---|---|---|---|---|---|---|---|---|
| Designation | HCVR | HCDR1 | HCDR2 | HCDR3 | LCVR | LCDR1 | LCDR2 | LCDR3 |
| H4H17855P | 1 | 5 | 6 | 7 | 2 | 8 | 9 | 10 |
| H4H17871P | 3 | 11 | 12 | 13 | 4 | 14 | 15 | 16 |

TABLE 2

| | | 60 nM | | | | |
| mAb | mAb Capture | hBMP6 Bound | $k_a$ | $k_d$ | $K_D$ | t1/2 |
| Captured | Level (RU) | (RU) | (1/Ms) | (1/s) | (M) | (min) |
|---|---|---|---|---|---|---|
| H4H17855P | 282 ± 2.4 | 72 | 1.78E+05 | 6.30E−05 | 3.55E−10 | 183 |
| H4H17871P | 243 ± 1.8 | 52 | 2.83E+05 | 4.14E−05 | 1.95E−10 | 279 |
| Isotype Control mAb | 345 ± 1.8 | 2 | NB | NB | NB | NB |

Binding kinetics parameters of hBMP6 binding to anti-BMP6 monoclonal antibodies at 25° C.

NB; no binding was observed under the current experimental conditions.

TABLE 3

| | | 60 nM | | | | |
| mAb | mAb Capture | hBMP6 Bound | $k_a$ | $k_d$ | $K_D$ | t1/2 |
| Captured | Level (RU) | (RU) | (1/Ms) | (1/s) | (M) | (min) |
|---|---|---|---|---|---|---|
| H4H17855P | 319 ± 9.3 | 83 | 6.11E+04 | 8.17E−05 | 1.34E−09 | 141 |
| H4H17871P | 286 ± 7.7 | 43 | 4.16E+04 | 1.00E−05 [#] | 2.40E−10 | 1155 |
| Isotype Control mAb | 407 ± 3.4 | 2 | NB | NB | NB | NB |

Binding kinetics parameters of hBMP6 binding to anti-BMP6 monoclonal antibodies at 37° C.

NB; no binding was observed under the current experimental conditions.

[#] under the current experimental conditions, no dissociation of hBMP6 was observed from the captured anti-BMP6 monoclonal antibody and $k_d$ value was manually fixed at 1.00E−05 when fitting the real time binding sensorgrams.

TABLE 4

| | | 60 nM | | | | |
| mAb | mAb Capture | mBMP6 Bound | $k_a$ | $k_d$ | $K_D$ | t1/2 |
| Captured | Level (RU) | (RU) | (1/Ms) | (1/s) | (M) | (min) |
|---|---|---|---|---|---|---|
| H4H17855P | 274 ± 4.8 | 41 | 3.66E+04 | 1.30E−04 | 3.55E−09 | 89 |
| H4H17871P | 237 ± 2.8 | 25 | 3.74E+04 | 1.27E−04 | 3.39E−09 | 91 |
| Isotype Control mAb | 346 ± 1.1 | 3 | NB | NB | NB | NB |

Binding kinetics parameters of mBMP6 binding to anti-BMP6 monoclonal antibodies at 25° C.

NB: no binding was observed under the current experimental conditions.

50

TABLE 5

| | | 60 nM | | | | |
| mAb | mAb Capture | mBMP6 Bound | $k_a$ | $k_d$ | $K_D$ | t1/2 |
| Captured | Level (RU) | (RU) | (1/Ms) | (1/s) | (M) | (min) |
|---|---|---|---|---|---|---|
| H4H17855P | 295 ± 3.7 | 46 | 2.38E+04 | 1.54E−04 | 6.46E−09 | 75 |
| H4H17871P | 288 ± 2.5 | 19 | 2.35E+04 | 9.43E−05 | 4.00E−09 | 123 |
| Isotype Control mAb | 408 ± 6.2 | 3 | NB | NB | NB | NB |

Binding kinetics parameters of mBMP6 binding to anti-BMP6 monoclonal antibodies at 37° C.

*NB indicates that no binding was observed under the current experimental conditions.

Example 4. Blocking of BMP6 Receptor Binding by Anti-BMP6 Monoclonal Antibodies Blocking of BMP6 from binding to its receptors, Hemojuvelin, ActR2A or ActR2B by anti-BMP6 monoclonal antibodies (mAbs) was determined using a real-time surface plasmon resonance (SPR) biosensor instrument, Biacore 3000. All binding studies were performed in 10 mM HEPES, 150 mM NaCl, 3 mM EDTA, 1 µg/mL Heparin, and 0.05% v/v Surfactant Tween-20, pH 7.4 (HBS-EHT) buffer at 25° C.

Approximately 10500, 5000 and 5000 RU of human Hemojuvelin expressed with a human Fc tag (hHJV-hFc; SEQ ID: 37), human ActR2A extracellular domain expressed with a C-terminal human Fc tag (hActR2A-hFc; SEQ ID: 38), human ActR2B extracellular domain expressed with a C-terminal human Fc tag (hActR2B-hFc; SEQ ID: 39), respectively were individually immobilized on different flow cells of CM4 sensor surface using the EDC/NHS surface chemistry; while the activated/deactivated surface was used as reference control surface. A concentration of 10 nM human BMP-6 was pre-mixed with 400 nM anti-BMP-6 mAbs for at least 2 hours before the start of the experiment. The mixture of BMP6 and anti-BMP6 mAbs was injected over different immobilized sensor surfaces for 10 minutes at a flow rate of 5 µL/min. The binding of 27 nM BMP6 to immobilized surfaces was used to assess percent blocking while the non-specific binding of anti-BMP6 mAbs without BMP6 was also tested.

As shown in Table 6, the anti-BMP6 antibodies of the invention demonstrated partial blocking of BMP6 binding to hHJV-hFc. The anti-BMP6 antibodies of the invention demonstrated enhanced binding of BMP6 to the hActR2A-hFc and hActR2B-hFc surfaces.

TABLE 6

Blocking of BMP6 from binding to its receptors, Hemojuvelin, ActR2A or ActR2B by anti-BMP6 monoclonal antibodies.

| | | H4H17855P | H4H17871P | Isotype Control mAb |
|---|---|---|---|---|
| hHJV-hFc Surface | 400 nM mAb Binding (RU) | 39 | 27 | 14 |
| | 400 nM mAb + 10 nM hBMP-6 Binding (RU) | 266 | 111 | 299 |
| | % Blocking | 61 | 84 | 41 |
| hActR2A-hFc Surface | 400 nM mAb Binding (RU) | 34 | 30 | 17 |
| | 400 nM mAb + 10 nM hBMP-6 Binding (RU) | 2490 | 659 | 246 |
| | % Blocking | −400 | −46 | 43 |
| hActR2B-hFc Surface | 400 nM mAb Binding (RU) | 37 | 28 | 15 |
| | 400 nM mAb + 10 nM hBMP-6 Binding (RU) | 2486 | 711 | 187 |
| | % Blocking | −563 | −94 | 25 |

Example 5. Anti-BMP6 Antibodies Blocking BMP6 Binding to Hemojuvelin and ActivinR2A The ability of anti-BMP6 monoclonal antibodies to block binding of human BMP6 to two natural binding partners, the co-receptor Hemojuvelin (HJV), and a type II binding receptor, Activin Receptor 2a (ActR2a), was measured using two competition sandwich ELISAs.

The human BMP6 protein used in the experiments was purchased from R&D systems (hBMP6; Cat ##507-BP/CF) and was biotinylated for detection purposes (biot-hBMP6) and the molecular weight of 30 kDa was used for calculations as BMP6 protein is naturally a dimer. The HJV protein used in the experiments was comprised of a portion of the human HJV extracellular domain (aa Gln36-Ser399) expressed with a linker sequence and the Fc portion of the human IgG1 at the C-terminus (hHJV-hFc; SEQ ID: 37) The Activin R2a protein was purchased from R&D Systems (hActR2a-hFc; R&D systems, Cat #340-RC2). An isotype antibody control, was included, along with a commercially available goat-anti-hBMP6 positive blocking control antibody (R&D Systems, Cat #AF507).

Experiments were carried out using the following procedure. Receptors were coated in Hank's Balanced Salt Solution (HBSS) separately at a concentration of 5 µg/mL for hHJV-hFc and 2.5 g/mL for hActR2a-hFc on a 96-well microtiter plate overnight at 4° C. Nonspecific binding sites were subsequently blocked using a 1.0% (w/v) solution of BSA in HBSS. In other microtiter plates, a constant amount of 2.5 nM of biot-BMP6 (for HJV capture) or 1.5 nM biot-BMP6 (for ActR2a capture) protein was titrated with anti-BMP6 antibodies or isotype control antibodies ranging from 5.1 pM to 300 nM in serial dilution in HBSS with 1.0% BSA and 3.33 g/mL heparin. These antibody-protein complexes, after a one-hour incubation, were transferred to the microtiter plate coated with hHJV-hFc or hActR2a-hFc. After two hours of incubation at room temperature, the wells were washed, and plate-bound biot-BMP6 was detected with neutravidin conjugated with horseradish peroxidase (HRP) (Thermo Scientific, Cat #31030). The plates were then developed using TMB substrate solution (BD Biosciences, Cat #555214) according to manufacturer's recommendation and absorbance at 450 nm was measured on a Victor X5 plate reader.

Data analysis was performed using a sigmoidal dose-response model within Prism™ software (GraphPad). The calculated $IC_{50}$ value, defined as the concentration of antibody required to reduce 50% of biot-BMP6 binding to hHJV-hFc or hActR2a-hFc, was used as an indicator of blocking potency. Percent blockade at indicated concentration of the antibody tested was calculated as an indicator of the ability of the antibodies to block the binding of 2.5 nM or 1.5 nM of biot-BMP6 to hHJV-hFc or hActR2a-hFc on the plate, respectively. In the calculation, binding signal of the sample of the constant biot-BMP6 without the presence of the antibody for each assay was referenced as 100% binding or 0% blocking; and the baseline signal of the sample of buffer only without the presence of biot-BMP6 was referenced as 0% binding or 100% blocking.

The blockade of each antibody at the maximum concentration of 300 nM antibody was calculated and compared. In addition, for the blocking of BMP6 binding to ActR2a, the blockade of each antibody at 11.1 nM was calculated and reported to reflect the enhanced binding signal of biot-BMP6 in the presence of some antibodies in this assay.

The blocking results of the two assays are summarized in Table 7. The two antibodies of the invention blocked >90% of 2.5 nM biot-BMP6 protein binding to hHJV-hFc with 300 nM of antibody. The blocking potency ($IC_{50}$value) of H4H17855P was calculated at 0.522 nM, which was below the lower limit of quantitation for the assay of 1.25 nM. The $IC_{50}$ value of H4H17871P blocking BMP6 protein binding to hHJV-hFc was 1.61 nM. The potency of the positive control anti-BMP6 commercial Ab was 2.32 nM with 93% blocking at 300 nM antibody. The Comparator Ab blocked with an $IC_{50}$ value of 2.99 nM with maximal blocking of 88%. The isotype control antibody blocked <30% at concentrations up to 300 nM antibody, as expected.

The two test antibodies, H4H17855P and H4H17871P, enhanced biot-BMP6 protein binding to hActR2a-hFc 29.8% and 15.5%, respectively at 11.1 nM, while blocking 19.5% and 37.3% at 300 nM antibody. The positive control anti-BMP6 commercial Ab blocked 92.8% with an $IC_{50}$ of 11.8 nM. The Comparator Ab blocked >30% at 300 nM, but did not have a sigmoidal curve so no $IC_{50}$ value was reported. The isotype control antibody blocked <30%, as expected.

TABLE 7

| | Blocking of 2.5 nM Biot-hBMP6 Binding to HJV-hFc IC50 (M) | 300 nM Ab Blocking of 2.5 nM Biot-hBMP6 Binding to HJV-hFc (%) | Blocking of 1.5 nM Biot-hBMP6 Binding to ActR2a-hFc IC50 (M) | 300 nM Ab Blocking of 1.5 nM Biot-hBMP6 Binding to ActR2a-hFc (%) | 11.1 nM Ab Blocking of 1.5 nM Biot-hBMP6 Binding to ActR2a-hFc (%) |
|---|---|---|---|---|---|
| Antibody | | | | | |
| H4H17855P | 5.22E−10* | 97.0 | Enhancer | 19.5 | −29.8 |
| H4H17871P | 1.61E−09 | 94.9 | Enhancer/Blocker | 37.3 | −15.5 |
| Controls | | | | | |
| Comparator Ab | 2.99E−09 | 88.2 | IC | 47.7 | −1.6 |
| ant-BMP6 commercial Ab | 2.32E−09 | 93.0 | 1.18E−08 | 92.8 | 53.7 |
| Isotype control Ab | NB | 26.3 | NB | 19.9 | 25.7 |

*Effect of anti-BMP6 antibodies in Blocking ELISA*

IC indicates inconclusive $IC_{50}$ value due to non-sigmoidal blocking curve

NB indicated non-blocking (<30%)

*indicates value below the lower limit of quantitation of 1.25E−09M for the BMP6 blocking HJV assay

Example 6. Binding Cross-Reactivity of Anti-BMP6 Monoclonal Antibodies

Binding cross-reactivity of anti-BMP6 monoclonal antibodies to BMP6 family members, (Human: BMP6, BMP5, BMP7, BMP8A, BMP9, BMP10, BMP12, BMP14, BMP3b, Activin A, and GDF3 and mouse: BMP6 and GDF6) was determined using a real-time Bio-Layer Interferometry (BLI) biosensor using Octet HTX instrument. All binding studies were performed in 10 mM HEPES, 150 mM NaCl, 3 mM EDTA, 1 mg/mL BSA, 50 µg/mL Heparin, and 0.05% v/v Surfactant Tween-20, pH 7.4 (HBS-EBHT) buffer at 25° C. with the plate shaking at a speed of 1000 rpm. To assess binding cross-reactivity, Protein A coated Octet biosensor (Pall ForteBio Corp., #18-5010) was first dipped in wells containing 20 µg/mL of anti-BMP6 monoclonal antibodies for 4 minutes followed by submerging in wells containing 100 nM of different BMP6 family members for 4 minutes. The biosensors were washed in HBS-EBHT buffer in between every step of the experiment. At the end of each cycle, the Protein A biosensor was regenerated using three alternate 5 second dips in 10 mM Glycine pH 2.0 and 10 second dip HBS-EBHT buffer. The real-time binding response was monitored during the course of the experiment and the binding response at the end of every step was recorded and tabulated as shown in Tables 8A and 8B.

TABLE 8A

Binding cross-reactivity of anti-BMP6 monoclonal antibodies.

| mAb Captured | mAb Capture Level (nm) | Human BMP6 | Mouse BMP6 | Human BMP7 | Human BMP8A | Human BMP9 | Human BMP10 |
|---|---|---|---|---|---|---|---|
| H4H17855P | 4.76 ± 0.19 | 0.29 | 0.09 | 0.05 | −0.02 | 0.00 | −0.01 |
| H4H17871P | 4.31 ± 0.14 | 0.21 | 0.09 | 0.00 | 0.00 | 0.01 | 0.01 |
| Isotype control mAb | 4.12 ± 0.06 | −0.05 | −0.06 | −0.05 | −0.05 | −0.03 | −0.04 |

TABLE 8B

Binding cross-reactivity of anti-BMP6 monoclonal antibodies.

| mAb Captured | Human BMP12/ GDF7 | Human BMP14/ GDF5 | Human BMP5 | Human Activin A | Human GDF3 | Mouse GDF6 | Human BMP3b |
|---|---|---|---|---|---|---|---|
| H4H17855P | 0.03 | −0.02 | 0.01 | −0.02 | 0.03 | −0.02 | 0.27 |
| H4H17871P | 0.01 | −0.01 | −0.01 | −0.01 | 0.03 | −0.02 | 0.19 |
| Isotype control mAb | −0.04 | −0.05 | −0.06 | −0.06 | −0.01 | −0.06 | 0.12 |

35

Example 7. Testing for Antibody Inhibition of BMP6 Activation in Bioassay with Hep3B/BRE-Luc Cells (Human BMP6) or W-20-17/BRE-Luc Cells (Mouse BMP6)

Cell lines were engineered to stably express a luciferase reporter [BMP-responsive element (BRE(2X)-luciferase-IRES-GFP)], and sorted for high expression of GFP to detect the regulation of BMP6 signaling. To test human BMP6 (hBMP6), Hep3B2.1-7 cells (referred to hereafter as Hep3B cells), a human hepatocellular carcinoma cell line was used and, to test mouse BMP6 (mBMP6), W-20-17 cells, a mouse bone marrow stromal cell line previously shown to be responsive to BMP2 (Thies et al. 1992), was used. The resulting reporter cell lines are referred to as Hep3B/BRE-luc and W-20-17/BRE-luc cells. Hep3B/BRE-luc cells were maintained in a media comprised of MEM, 10% FBS, Penicillin/Streptomycin, L-Glutamine, NEAA and Sodium Pyruvate (this media is referred to Hep3B Media) and W-20-17/BRE-luc cells were maintained in a media comprised of 10% FBS, DMEM, Penicillin/Streptomycin/L-Glutamine, and 200 ug/ml G418 (this media is referred to W-20-17 Media).

For the hBMP6 bioassay, Hep3B/BRE-luc cells were seeded onto 96-well assay plates in Hep3B media at 10,000 cells/well and incubated at 37° C. in 5% $CO_2$ overnight. The next day, the Hep3B media was removed from the Hep3B cells and replaced with media comprised of MEM, 1% FBS, Penicillin/Streptomycin, L-Glutamine, NEAA and Sodium Pyruvate, and then incubated at 37° C. in 5% $CO_2$ for an additional 6 hours before BMP6 and antibodies diluted in the assay media (media comprised of MEM, 0.1% BSA, Penicillin/Streptomycin+L-Glutamine) were added to the cells. For the mBMP6 bioassay, W-20-17/BRE-luc cells were seeded onto 96-well assay plates in W-20-17 media at 10,000 cells/well and incubated at 37° C. in 5% $CO_2$ overnight. BMP6 and antibodies were added to the cells the following day in assay media comprised of DMEM, 0.1% BSA and Penicillin/Streptomycin/L-Glutamine.

For BMP6 activation, human BMP6 (hBMP6; R&D systems, Cat #507-BP/CF) or mouse BMP6 (mBMP6; R&D systems, Cat #6325-BM/CF) was serially diluted 1:3 from 300 nM to 0.005 nM, and added to cells including a no BMP6 control for dose responses. For antibody inhibition of BMP6, antibodies were serially diluted at 1:3 from either 1000 nM to 0.02 nM or 100 nM to 0.002 nM and mixed with either 1 nM of hBMP6 or 5 nM of mBMP6. A no antibody control was included in all antibody dose responses. These antibody/BMP6 mixtures were then incubated at 25° C. for 30 minutes and added to the cells. Cells were incubated at 37° C. and 5% $CO_2$ overnight for Hep3B/BRE-luc cells or 5.5 hours for W-20-17/BRE-luc cells. At the conclusion of these incubations, cells were incubated at 25° C. for 15 minutes, followed by addition of OneGlo™ reagent (Promega E6130) to measure the amount of luciferase present in cells. Plates were read for luminescence by a Victor™ X instrument (Perkin Elmer) 4 minutes after the addition of OneGlo™ with the results being analyzed using nonlinear regression (4-parameter logistics) with Prism6 software (GraphPad) to obtain $EC_{50}$ and $IC_{50}$ values. Inhibition of antibodies was calculated such that 0-100% inhibition is the range of inhibition of either 1-1 nM hBMP6 or 0-5 nM mBMP6 without inhibitor.

As shown in Table 9, both of the anti-BMP6 antibodies of the invention demonstrated complete inhibition of 1 nM hBMP6 mediated activation of Hep3B/BRE-luc cells. The $IC_{50}$ values of the hBMP6 inhibition ranged from 0.25 nM to 1.6 nM. Comparator Ab demonstrated complete inhibition of 1 nM hBMP6 with an $IC_{50}$ value of 0.53 nM. A dose response of hBMP6 activated Hep3B/BRE-luc cells with $EC_{50}$ values of 0.94 nM and 0.33 nM.

As shown in Table 9, both of the anti-BMP6 antibodies of the invention demonstrated complete inhibition of 5 nM mBMP6 mediated activation of W-20-17/BRE-luc cells. The $IC_{50}$ values of the mBMP6 inhibition ranged from 1.9 nM to 11 nM. Comparator Ab demonstrated complete inhibition of 5 nM mBMP6 with an $IC_{50}$ of 1.9 nM. A dose response of mBMP6 activated W-20-17/BRE-luc cells with $EC_{50}$ values of 1.2 nM and 1.3 nM.

An isotype control antibody demonstrated no inhibition of either human BMP6 or mouse BMP6.

TABLE 9

| Anti-BMP6 antibody inhibition of BMP6 activation in cell-based assays | | | | |
|---|---|---|---|---|
| BMP6 | Human | | Mouse | |
| Cell Line | Hep3B/BRE-luc | | W-20-17/BRE-IUC | |
| $EC_{50}$ [M] of BMP6 | 9.4E−10 | 3.3E−10 | 1.2E−09 | 1.3E−09 |
| Constant concentration of BMP6 | 1 nM | | 5 nM | |
| Antibody | $IC_{50}$ [M] | $IC_{50}$ [M] | $IC_{50}$ [M] | $IC_{50}$ [M] |
| H4H17871P | 1.6E−09 | Not Tested | 1.1E−08 | Not Tested |
| H4H17855P | 2.5E−10 | Not Tested | 1.9E−09 | Not Tested |
| Comparator Ab | Not Tested | 5.3E−10 | Not Tested | 1.9E−09 |
| Isotype control | No Inhibition | No Inhibition | No Inhibition | No Inhibition |

Example 8. Mouse Experiment In Vivo, Serum Hepcidin and Iron Levels after Bmp6 Antibody Treatment (H4H17855P)

To determine the efficacy of a BMP6 antibody of the invention in increasing serum and decreasing serum Hepcidin, an in vivo experiment was performed in mice homozygous for the expression of human BMP6 and HJV in place of mouse BMP6 and HJV. For the study, 5 or 6 mice per group received 2 doses of antibody on day 1 and 3 at either 10 or 20 mg/kg. Mice were sacrificed on day 5 and serum was taken to measure hepcidin and iron levels.

Figure 2:
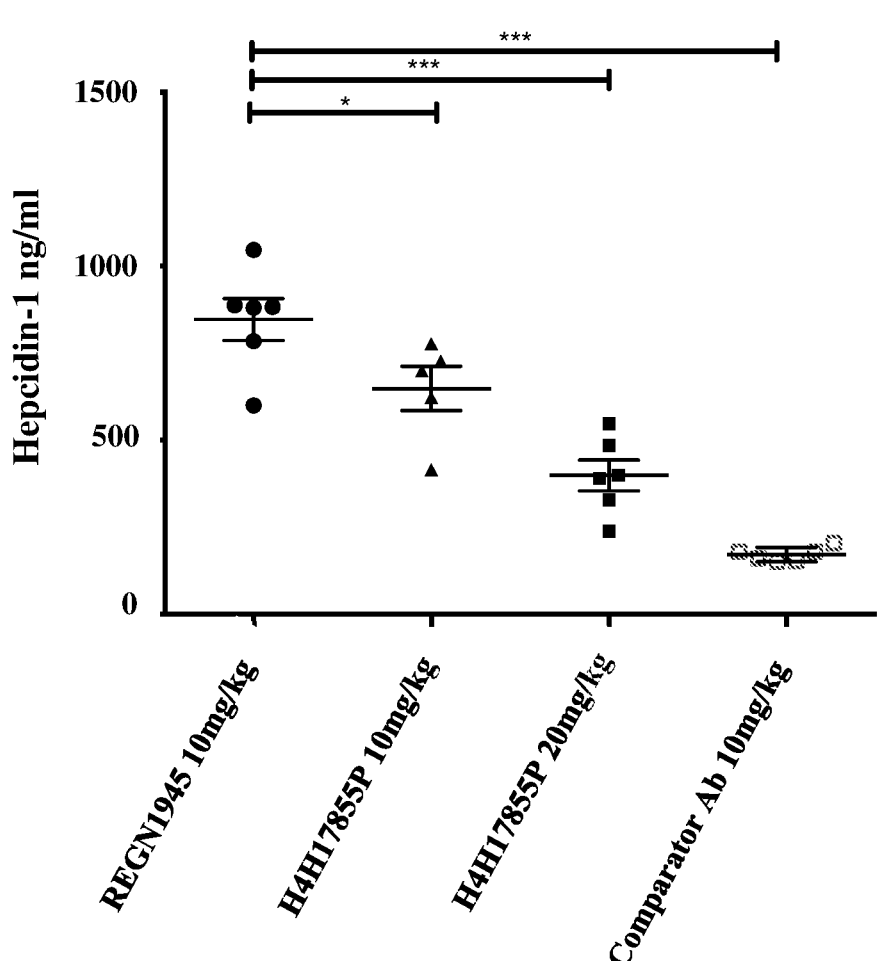
FIG. 2 shows mice receiving a BMP6 antibody of the invention, H4H17855P, had decreased serum hepcidin compared to mice receiving an isotype control antibody at 10 mg/kg. There is a dose dependent effect of the BMP6 antibody, which demonstrated decreased hepcidin at 20 mg/kg as compared to 10 mg/kg.

As shown in Table 10 and FIGS. 1 and 2, mice receiving a BMP6 antibody of the invention, H4H17855P, had increased serum iron and decreased serum hepcidin compared to mice receiving an isotype control antibody at 10 mg/kg. There is a dose dependent effect of the BMP6 antibody, which demonstrated increased serum iron and decreased Hepcidin at 20 mg/kg as compared to 10 mg/kg

TABLE 10

Effect of a BMP6 antibody on serum iron and Hepcidin in vivo

| Antibody | dose | n | Serum iron (mean) | Serum iron (standard deviation) | Serum hepcidin (mean) | Serum hepcidin (standard deviation) |
|---|---|---|---|---|---|---|
| Isotype control | 10 mg/kg | 6 | 208.3 | 105 | 847.3 | 147.7 |
| H4H17855P | 10 mg/kg | 5 | 306.1 | 161.5 | 648.5 | 141.9 |
| H4H17855P | 20 mg/kg | 6 | 425.5 | 118.9 | 398.7 | 109.1 |
| Comparator Ab | 10 mg/kg | 6 | 385.0 | 228.5 | 171.7 | 20.57 |

Example 9. Mouse Experiment In Vivo, Serum Hepcidin and Iron Levels after Bmp6 Antibody Treatment (H4H17871P)

To determine the efficacy of a BMP6 antibody of the invention in increasing serum and decreasing serum Hepcidin, an in vivo experiment was performed in mice homozygous for the expression of human BMP6 and HJV in place of mouse BMP6 and HJV. For the study, 7 mice per group received one s.c. dose of 5 mg/kg of antibody at day 1. Mice were sacrificed at day 5 and serum was taken to measure hepcidin and iron levels.

Serum iron levels were measured using the QuantiChrom Iron Assay Kit (BioAssay Systems DIFE-250). Serum Hepcidin was measured using the Hepcidin Murine-Compete ELISA kit (Intrinsic Lifesciences HMC-001)

Figure 3:
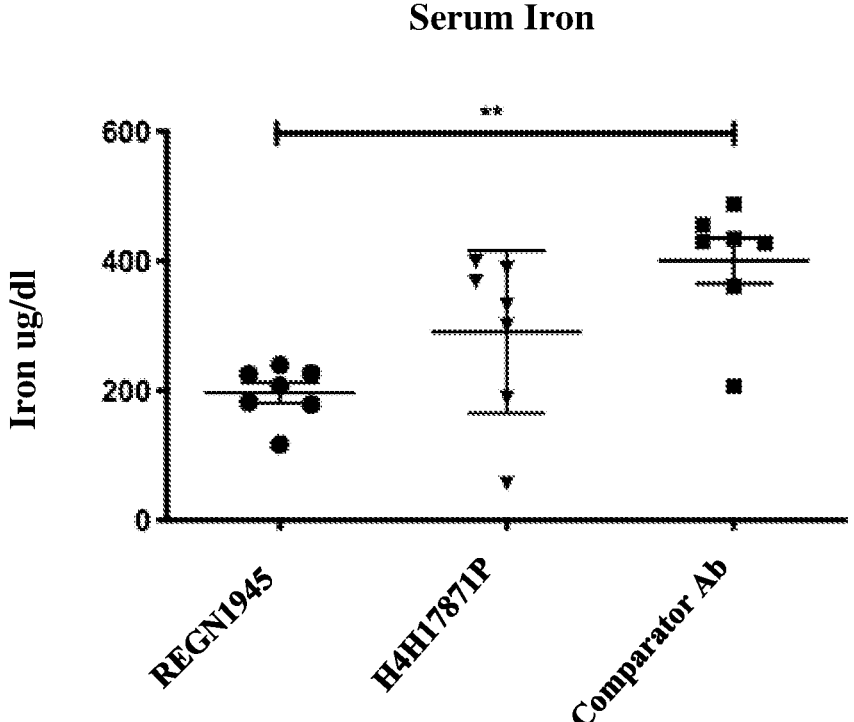
FIG. 3 shows that mice receiving a BMP6 antibody of the invention, H4H17871P, had increased serum iron compared to mice receiving an isotype control antibody.
Figure 4:
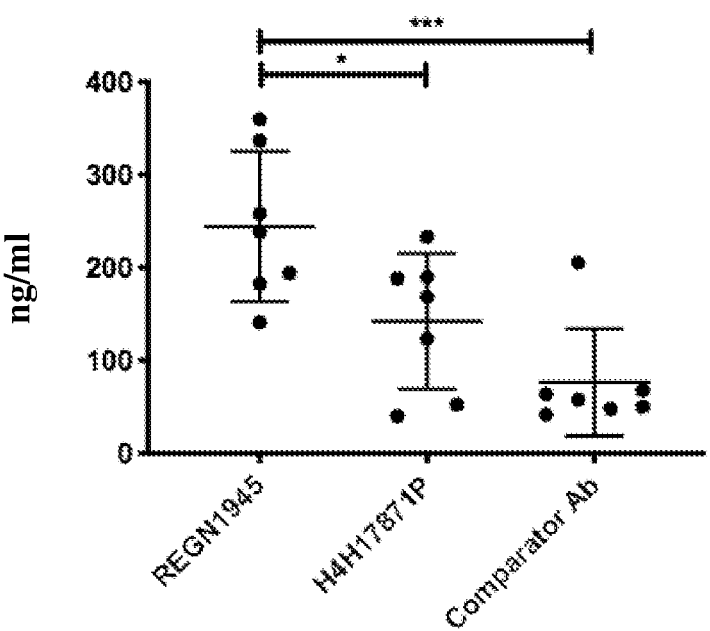
FIG. 4 shows that mice receiving a BMP6 antibody of the invention, H4H17871P, had decreased serum hepcidin compared to mice receiving an isotype control antibody.

As shown in Table 11 and FIGS. 3 and 4, mice receiving a BMP6 antibody of the invention, H4H17871P, had increased serum iron and decreased serum hepcidin compared to mice receiving an isotype control antibody.

TABLE 11

Effect of a BMP6 antibody on serum iron and Hepcidin in vivo

| Antibody | Dose | n | Serum iron (mean) | Serum iron (standard deviation) | Serum hepcidin (mean) | Serum hepcidin (standard deviation) |
|---|---|---|---|---|---|---|
| Isotype control | 5 mg/kg | 7 | 196.7 | 42.1 | 244.4 | 80.75 |
| H4H17871P | 5 mg/kg | 7 | 290.6 | 125.6 | 142.3 | 73.24 |
| Comparator Ab | 5 mg/kg | 7 | 400.4 | 93.52 | 76.37 | 57.7 |

What is claimed is:

1. An isolated human monoclonal antibody or antigen-binding fragment thereof that binds specifically to human bone morphogenetic protein 6 (BMP6), wherein the antibody or antigen-binding fragment comprises:

(i)
(a) a heavy chain complementarity determining region (HCDR) 1 domain comprising SEQ ID NO: 5;
(b) a HCDR2 domain comprising SEQ ID NO: 6;
(c) a HCDR3 domain comprising SEQ ID NO: 7;
(d) a light chain complementarity determining region (LCDR) 1 domain comprising SEQ ID NO: 8;
(e) a LCDR2 domain comprising SEQ ID NO: 9; and
(f) a LCDR3 domain comprising SEQ ID NO: 10; or (ii)
(a) a HCDR1 domain comprising SEQ ID NO: 11;
(b) a HCDR2 domain comprising SEQ ID NO: 12;
(c) a HCDR3 domain comprising SEQ ID NO: 13;
(d) a LCDR 1 domain comprising SEQ ID NO: 14;
(e) a LCDR2 domain comprising SEQ ID NO: 15; and
(f) a LCDR3 domain comprising SEQ ID NO: 16.

2. The isolated human antibody or antigen-binding fragment of claim 1, wherein the antibody or antigen-binding fragment comprises a heavy chain variable region comprising the amino acid sequence set forth in SEQ ID NO: 1 and a light chain variable region comprising the amino acid sequence set forth in SEQ ID NO: 2.

3. The isolated human antibody or antigen-binding fragment of claim 1, wherein the antibody or antigen-binding fragment comprises a light chain comprising the amino acid sequence set forth in SEQ ID NO: 34, and a heavy chain comprising the amino acid sequence set forth in SEQ ID NO: 33.

4. The antigen-binding fragment of claim 1, wherein the antigen-binding fragment is a Fab fragment, a F(ab')₂ fragment, a Fd fragment, a Fv fragment, a single-chain Fv (scFv) molecule, or a dAb fragment.

5. A method for making an antibody or antigen-binding fragment of claim 1 comprising:

(i) introducing one or more polynucleotides encoding a light immunoglobulin chain of said antibody or fragment and a heavy immunoglobulin chain of said antibody or fragment into a host cell;

(ii) culturing the host cell a growth medium under conditions favorable to expression of the polynucleotide(s); and (iii) optionally, isolating the antibody or fragment from the host cell and/or medium in which the host cell is grown.

6. An injection device or vessel comprising an antibody or antigen-binding fragment of claim 1.

7. A pharmaceutical composition comprising an isolated human antibody or antigen-binding fragment thereof that binds to human BMP6 according to claim 1, and a pharmaceutically acceptable carrier or diluent.

8. A method for preventing or treating an iron-deficiency anemia or an iron-deficiency related disorder in a patient in need thereof, comprising administering an effective amount of an antibody or an antigen-binding fragment thereof according to claim 1 to the patient.

9. The method of claim 8, wherein the antibody or antigen-binding fragment thereof is administered subcutaneously, intravenously, intradermally, orally, or intramuscularly.

10. The method of claim 8, wherein the iron-deficiency anemia or an iron-deficiency related disorder produces a condition selected from the group consisting of extreme fatigue, weakness, pale skin, chest pain, fast heartbeat, heart palpitations, shortness of breath, headache, dizziness, light-headedness, cold hands, cold feet, inflammation of the tongue and restless legs;

and administration of the antibody or antigen-binding fragment treats the condition or reduces the severity of one or more symptoms of the condition.

11. The isolated human antibody or antigen-binding fragment of claim 1, wherein the antibody or antigen-binding fragment comprises a heavy chain variable region comprising the amino acid sequence set forth in SEQ ID NO: 3 and a light chain variable region comprising the amino acid sequence set forth in SEQ ID NO: 4.

12. The isolated human antibody or antigen-binding fragment of claim 1, wherein the antibody or antigen-binding fragment comprises a light chain comprising the amino acid sequence set forth in SEQ ID NO: 36, and a heavy chain comprising the amino acid sequence set forth in SEQ ID NO: 35.

13. The pharmaceutical composition of claim 7, further comprising one or more additional therapeutic agents.

14. The pharmaceutical composition of claim 13, wherein the additional therapeutic agent is an iron supplement.

* * * * *

SEQUENCE LISTING

<160> NUMBER OF SEQ ID NOS: 43

<210> SEQ ID NO 1
<211> LENGTH: 118
<212> TYPE: PRT
<213> ORGANISM: Artificial Sequence
<220> FEATURE:
<223> OTHER INFORMATION: Synthetic

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Arg Thr Tyr Tyr Thr Asp Ser Val
    50                  55                  60

Lys Gly Arg Phe Thr Met Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Arg Pro Tyr Asn Ser Pro Phe Asp Pro Trp Gly Gln Gly Thr
            100                 105                 110

Leu Val Thr Val Ser Ser
            115

<210> SEQ ID NO 2

```
<211> LENGTH: 108
<212> TYPE: PRT
<213> ORGANISM: Artificial Sequence
<220> FEATURE:
<223> OTHER INFORMATION: Synthetic

<400> SEQUENCE: 2

Glu Ile Val Leu Thr Gln Ser Pro Gly Thr Leu Ser Leu Ser Pro Gly
1               5                   10                  15

Glu Gly Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Val Val Tyr Tyr Cys Gln His Phe Gly Gly Thr Pro
                85                  90                  95

Phe Thr Phe Gly Gly Gly Thr Lys Val Glu Ile Lys
            100                 105

<210> SEQ ID NO 3
<211> LENGTH: 118
<212> TYPE: PRT
<213> ORGANISM: Artificial Sequence
<220> FEATURE:
<223> OTHER INFORMATION: Synthetic

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Asp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Ser Arg Ser Ser Pro Phe Asp Pro Trp Gly Gln Gly Thr
            100                 105                 110

Leu Val Thr Val Ser Ser
        115

<210> SEQ ID NO 4
<211> LENGTH: 107
<212> TYPE: PRT
<213> ORGANISM: Artificial Sequence
<220> FEATURE:
<223> OTHER INFORMATION: Synthetic

<400> SEQUENCE: 4

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30
```

```
Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Phe Tyr Ser Trp
                85                  90                  95

Thr Phe Gly Gln Gly Thr Lys Val Glu Ile Lys
                100                 105
```

<210> SEQ ID NO 5
<211> LENGTH: 8
<212> TYPE: PRT
<213> ORGANISM: Artificial Sequence
<220> FEATURE:
<223> OTHER INFORMATION: Synthetic

<400> SEQUENCE: 5

```
Gly Phe Thr Phe Ser Ser Tyr Ala
1               5
```

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

```
Ile Ser Gly Ser Gly Gly Arg Thr
1               5
```

<210> SEQ ID NO 7
<211> LENGTH: 11
<212> TYPE: PRT
<213> ORGANISM: Artificial Sequence
<220> FEATURE:
<223> OTHER INFORMATION: Synthetic

<400> SEQUENCE: 7

```
Ala Lys Arg Pro Tyr Asn Ser Pro Phe Asp Pro
1               5               10
```

<210> SEQ ID NO 8
<211> LENGTH: 7
<212> TYPE: PRT
<213> ORGANISM: Artificial Sequence
<220> FEATURE:
<223> OTHER INFORMATION: Synthetic

<400> SEQUENCE: 8

```
Gln Ser Val Ser Ser Ser Tyr
1               5
```

<210> SEQ ID NO 9
<211> LENGTH: 3
<212> TYPE: PRT
<213> ORGANISM: Artificial Sequence
<220> FEATURE:
<223> OTHER INFORMATION: Synthetic

<400> SEQUENCE: 9

```
Gly Ala Ser
1
```

```
<210> SEQ ID NO 10
<211> LENGTH: 9
<212> TYPE: PRT
<213> ORGANISM: Artificial Sequence
<220> FEATURE:
<223> OTHER INFORMATION: Synthetic

<400> SEQUENCE: 10

Gln His Phe Gly Gly Thr Pro Phe Thr
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic

<400> SEQUENCE: 11

Gly Phe Thr Phe Asn Asn Tyr Ala
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic

<400> SEQUENCE: 12

Ile Ser Gly Ser Gly Asp Ser Thr
1               5

<210> SEQ ID NO 13
<211> LENGTH: 11
<212> TYPE: PRT
<213> ORGANISM: Artificial Sequence
<220> FEATURE:
<223> OTHER INFORMATION: Synthetic

<400> SEQUENCE: 13

Ala Lys Arg Ser Arg Ser Ser Pro Phe Asp Pro
1               5                   10

<210> SEQ ID NO 14
<211> LENGTH: 6
<212> TYPE: PRT
<213> ORGANISM: Artificial Sequence
<220> FEATURE:
<223> OTHER INFORMATION: Synthetic

<400> SEQUENCE: 14

Gln Ser Ile Ser Ser Trp
1               5

<210> SEQ ID NO 15
<211> LENGTH: 3
<212> TYPE: PRT
<213> ORGANISM: Artificial Sequence
<220> FEATURE:
<223> OTHER INFORMATION: Synthetic

<400> SEQUENCE: 15

Lys Ala Ser
1
```

```
<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Gln Tyr Asn Phe Tyr Ser Trp Thr
1               5

<210> SEQ ID NO 17
<211> LENGTH: 354
<212> TYPE: DNA
<213> ORGANISM: Artificial Sequence
<220> FEATURE:
<223> OTHER INFORMATION: Synthetic

<400> SEQUENCE: 17
gaggtgcagc tggtggagtc tggggggaggc ttggtacagc cggggggggtc cctgagactc     60 tcctgtgcag cctctggatt cacgttcagt agctatgcca tgagttgggt ccgccaggct    120
ccagggaagg ggctggagtg ggtctccgct attagtggca gtggtggtag aacatactat    180
acagactccg tgaagggccg gttcaccatg tccagagaca attccaagaa cacgctgtat    240
ctgcaaatga acagcctgag agccgaggac acggccgtat attactgtgc gaagcgcccc    300
tataatagcc cgttcgaccc ctgggggccag ggaaccctgg tcaccgtctc ctca          354

<210> SEQ ID NO 18
<211> LENGTH: 324
<212> TYPE: DNA
<213> ORGANISM: Artificial Sequence
<220> FEATURE:
<223> OTHER INFORMATION: Synthetic

<400> SEQUENCE: 18
gaaatagtgt tgacgcagtc tccaggcacc ctgtctttgt ctccagggga aggagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgtagtgta ttactgccag cactttggtg gcacaccgtt cactttcggc    300
ggagggacca aggtggagat caaa                                           324

<210> SEQ ID NO 19
<211> LENGTH: 354
<212> TYPE: DNA
<213> ORGANISM: Artificial Sequence
<220> FEATURE:
<223> OTHER INFORMATION: Synthetic

<400> SEQUENCE: 19
gaggtgcagc tggtggagtc tggggggaggc ttggtacagc ctgggggggtc cctgagactc     60 tcctgtgcag cctctggatt cacctttaac aactatgcca tgagctgggt ccgccaggct    120
ccagggaagg ggctggagtg ggtctcagct attagtggta gtggtgatag cacatactac    180
gcagactccg tgaagggccg gttcaccatc tccagagaca attccaagaa cacgctgtat    240
ctgcaaatga acagcctgag agccgaggac acggccgtat attactgtgc gaaaaggagt    300
aggtcgtccc cgttcgaccc ctgggggccag ggaaccctgg tcaccgtctc ctca          354
```

```
<210> SEQ ID NO 20
<211> LENGTH: 321
<212> TYPE: DNA
<213> ORGANISM: Artificial Sequence
<220> FEATURE:
<223> OTHER INFORMATION: Synthetic

<400> SEQUENCE: 20
gacatccaga tgacccagtc tccttccacc ctgtctgcat ctgtaggaga cagagtcacc      60
atcacttgcc gggccagtca gagtattagt agctggttgg cctggtatca gcagaaacca     120
gggaaagccc ctaagctcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tataattttt attcgtggac gttcggccaa     300
gggaccaagg tggaaatcaa a                                                321

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
ggattcacgt tcagtagcta tgcc                                              24

<210> SEQ ID NO 22
<211> LENGTH: 24
<212> TYPE: DNA
<213> ORGANISM: Artificial Sequence
<220> FEATURE:
<223> OTHER INFORMATION: Synthetic

<400> SEQUENCE: 22
attagtggca gtggtggtag aaca                                              24

<210> SEQ ID NO 23
<211> LENGTH: 33
<212> TYPE: DNA
<213> ORGANISM: Artificial Sequence
<220> FEATURE:
<223> OTHER INFORMATION: Synthetic

<400> SEQUENCE: 23
gcgaagcgcc cctataatag cccgttcgac ccc                                    33

<210> SEQ ID NO 24
<211> LENGTH: 21
<212> TYPE: DNA
<213> ORGANISM: Artificial Sequence
<220> FEATURE:
<223> OTHER INFORMATION: Synthetic

<400> SEQUENCE: 24
cagagtgtta gcagcagcta c                                                 21

<210> SEQ ID NO 25
<211> LENGTH: 9
<212> TYPE: DNA
<213> ORGANISM: Artificial Sequence
<220> FEATURE:
<223> OTHER INFORMATION: Synthetic

<400> SEQUENCE: 25
```

-continued ggtgcatcc                                                              9

```
<210> SEQ ID NO 26
<211> LENGTH: 27
<212> TYPE: DNA
<213> ORGANISM: Artificial Sequence
<220> FEATURE:
<223> OTHER INFORMATION: Synthetic

<400> SEQUENCE: 26
```
cagcactttg gtggcacacc gttcact                                          27

```
<210> SEQ ID NO 27
<211> LENGTH: 24
<212> TYPE: DNA
<213> ORGANISM: Artificial Sequence
<220> FEATURE:
<223> OTHER INFORMATION: Synthetic

<400> SEQUENCE: 27
```
ggattcacct ttaacaacta tgcc                                             24

```
<210> SEQ ID NO 28
<211> LENGTH: 24
<212> TYPE: DNA
<213> ORGANISM: Artificial Sequence
<220> FEATURE:
<223> OTHER INFORMATION: Synthetic

<400> SEQUENCE: 28
```
attagtggta gtggtgatag caca                                             24

```
<210> SEQ ID NO 29
<211> LENGTH: 33
<212> TYPE: DNA
<213> ORGANISM: Artificial Sequence
<220> FEATURE:
<223> OTHER INFORMATION: Synthetic

<400> SEQUENCE: 29
```
gcgaaaagga gtaggtcgtc cccgttcgac ccc                                   33

```
<210> SEQ ID NO 30
<211> LENGTH: 18
<212> TYPE: DNA
<213> ORGANISM: Artificial Sequence
<220> FEATURE:
<223> OTHER INFORMATION: Synthetic

<400> SEQUENCE: 30
```
cagagtatta gtagctgg                                                    18

```
<210> SEQ ID NO 31
<211> LENGTH: 9
<212> TYPE: DNA
<213> ORGANISM: Artificial Sequence
<220> FEATURE:
<223> OTHER INFORMATION: Synthetic

<400> SEQUENCE: 31
``` aaggcgtct                                                              9

```
<210> SEQ ID NO 32
<211> LENGTH: 27
<212> TYPE: DNA
```

<213> ORGANISM: Artificial Sequence
<220> FEATURE:
<223> OTHER INFORMATION: Synthetic

<400> SEQUENCE: 32
caacagtata attttttattc gtggacg                                                      27

<210> SEQ ID NO 33
<211> LENGTH: 445
<212> TYPE: PRT
<213> ORGANISM: Artificial Sequence
<220> FEATURE:
<223> OTHER INFORMATION: Synthetic

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Arg Thr Tyr Tyr Thr Asp Ser Val
    50                  55                  60

Lys Gly Arg Phe Thr Met Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Pro Tyr Asn Ser Pro Phe Asp Pro Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys

```
              325                330                335

Ala Lys Gly Gln Pro Arg Glu Pro Gln Val Tyr Thr Leu Pro Pro Ser
          340                345                350

Gln Glu Glu Met Thr Lys Asn Gln Val Ser Leu Thr Cys Leu Val Lys
          355                360                365

Gly Phe Tyr Pro Ser Asp Ile Ala Val Glu Trp Glu Ser Asn Gly Gln
          370                375                380

Pro Glu Asn Asn Tyr Lys Thr Thr Pro Pro Val Leu Asp Ser Asp Gly
385                390                395                400

Ser Phe Phe Leu Tyr Ser Arg Leu Thr Val Asp Lys Ser Arg Trp Gln
              405                410                415

Glu Gly Asn Val Phe Ser Cys Ser Val Met His Glu Ala Leu His Asn
          420                425                430

His Tyr Thr Gln Lys Ser Leu Ser Leu Ser Leu Gly Lys
          435                440                445
```

<210> SEQ ID NO 34
<211> LENGTH: 215
<212> TYPE: PRT
<213> ORGANISM: Artificial Sequence
<220> FEATURE:
<223> OTHER INFORMATION: Synthetic

<400> SEQUENCE: 34

```
Glu Ile Val Leu Thr Gln Ser Pro Gly Thr Leu Ser Leu Ser Pro Gly
1                5                10                15

Glu Gly Ala Thr Leu Ser Cys Arg Ala Ser Gln Ser Val Ser Ser Ser
              20                25                30

Tyr Leu Ala Trp Tyr Gln Gln Lys Pro Gly Gln Ala Pro Arg Leu Leu
          35                40                45

Ile Tyr Gly Ala Ser Ser Arg Ala Thr Gly Ile Pro Asp Arg Phe Ser
      50                55                60

Gly Ser Gly Ser Gly Thr Asp Phe Thr Leu Thr Ile Ser Arg Leu Glu
65                70                75                80

Pro Glu Asp Phe Val Val Tyr Tyr Cys Gln His Phe Gly Gly Thr Pro
              85                90                95

Phe Thr Phe Gly Gly Gly Thr Lys Val Glu Ile Lys Arg Thr Val Ala
          100                105                110

Ala Pro Ser Val Phe Ile Phe Pro Pro Ser Asp Glu Gln Leu Lys Ser
          115                120                125

Gly Thr Ala Ser Val Val Cys Leu Leu Asn Asn Phe Tyr Pro Arg Glu
          130                135                140

Ala Lys Val Gln Trp Lys Val Asp Asn Ala Leu Gln Ser Gly Asn Ser
145                150                155                160

Gln Glu Ser Val Thr Glu Gln Asp Ser Lys Asp Ser Thr Tyr Ser Leu
              165                170                175

Ser Ser Thr Leu Thr Leu Ser Lys Ala Asp Tyr Glu Lys His Lys Val
          180                185                190

Tyr Ala Cys Glu Val Thr His Gln Gly Leu Ser Ser Pro Val Thr Lys
          195                200                205

Ser Phe Asn Arg Gly Glu Cys
          210                215
```

<210> SEQ ID NO 35
<211> LENGTH: 445
<212> TYPE: PRT

-continued

```
<213> ORGANISM: Artificial Sequence
<220> FEATURE:
<223> OTHER INFORMATION: Synthetic

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Asp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Ser Arg Ser Ser Pro Phe Asp Pro Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
```

```
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly Lys
                435                 440                 445

<210> SEQ ID NO 36
<211> LENGTH: 214
<212> TYPE: PRT
<213> ORGANISM: Artificial Sequence
<220> FEATURE:
<223> OTHER INFORMATION: Synthetic

<400> SEQUENCE: 36

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Phe Tyr Ser Trp
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 37
<211> LENGTH: 594
<212> TYPE: PRT
<213> ORGANISM: Artificial Sequence
<220> FEATURE:
<223> OTHER INFORMATION: Synthetic

<400> SEQUENCE: 37

Gln Cys Lys Ile Leu Arg Cys Asn Ala Glu Tyr Val Ser Ser Thr Leu
1               5                   10                  15

Ser Leu Arg Gly Gly Gly Ser Ser Gly Ala Leu Arg Gly Gly Gly Gly
            20                  25                  30
```

-continued

```
Gly Gly Arg Gly Gly Gly Val Gly Ser Gly Gly Leu Cys Arg Ala Leu
        35              40              45

Arg Ser Tyr Ala Leu Cys Thr Arg Arg Thr Ala Arg Thr Cys Arg Gly
    50              55              60

Asp Leu Ala Phe His Ser Ala Val His Gly Ile Glu Asp Leu Met Ile
65              70              75              80

Gln His Asn Cys Ser Arg Gln Gly Pro Thr Ala Pro Pro Pro Pro Arg
                85              90              95

Gly Pro Ala Leu Pro Gly Ala Gly Ser Gly Leu Pro Ala Pro Asp Pro
            100             105             110

Cys Asp Tyr Glu Gly Arg Phe Ser Arg Leu His Gly Arg Pro Pro Gly
            115             120             125

Phe Leu His Cys Ala Ser Phe Gly Asp Pro His Val Arg Ser Phe His
    130             135             140

His His Phe His Thr Cys Arg Val Gln Gly Ala Trp Pro Leu Leu Asp
145             150             155             160

Asn Asp Phe Leu Phe Val Gln Ala Thr Ser Ser Pro Met Ala Leu Gly
                165             170             175

Ala Asn Ala Thr Ala Thr Arg Lys Leu Thr Ile Ile Phe Lys Asn Met
            180             185             190

Gln Glu Cys Ile Asp Gln Lys Val Tyr Gln Ala Glu Val Asp Asn Leu
            195             200             205

Pro Val Ala Phe Glu Asp Gly Ser Ile Asn Gly Gly Asp Arg Pro Gly
    210             215             220

Gly Ser Ser Leu Ser Ile Gln Thr Ala Asn Pro Gly Asn His Val Glu
225             230             235             240

Ile Gln Ala Ala Tyr Ile Gly Thr Thr Ile Ile Ile Arg Gln Thr Ala
                245             250             255

Gly Gln Leu Ser Phe Ser Ile Lys Val Ala Glu Asp Val Ala Met Ala
            260             265             270

Phe Ser Ala Glu Gln Asp Leu Gln Leu Cys Val Gly Gly Cys Pro Pro
    275             280             285

Ser Gln Arg Leu Ser Arg Ser Glu Arg Asn Arg Arg Gly Ala Ile Thr
    290             295             300

Ile Asp Thr Ala Arg Arg Leu Cys Lys Glu Gly Leu Pro Val Glu Asp
305             310             315             320

Ala Tyr Phe His Ser Cys Val Phe Asp Val Leu Ile Ser Gly Asp Pro
                325             330             335

Asn Phe Thr Val Ala Ala Gln Ala Ala Leu Glu Asp Ala Arg Ala Phe
            340             345             350

Leu Pro Asp Leu Glu Lys Leu His Leu Phe Pro Ser Gly Pro Gly Asp
            355             360             365

Lys Thr His Thr Cys Pro Pro Cys Pro Ala Pro Glu Leu Leu Gly Gly
    370             375             380

Pro Ser Val Phe Leu Phe Pro Pro Lys Pro Lys Asp Thr Leu Met Ile
385             390             395             400

Ser Arg Thr Pro Glu Val Thr Cys Val Val Val Asp Val Ser His Glu
                405             410             415

Asp Pro Glu Val Lys Phe Asn Trp Tyr Val Asp Gly Val Glu Val His
            420             425             430

Asn Ala Lys Thr Lys Pro Arg Glu Glu Gln Tyr Asn Ser Thr Tyr Arg
            435             440             445

Val Val Ser Val Leu Thr Val Leu His Gln Asp Trp Leu Asn Gly Lys
```

-continued

```
            450             455             460
Glu Tyr Lys Cys Lys Val Ser Asn Lys Ala Leu Pro Ala Pro Ile Glu
465             470             475             480

Lys Thr Ile Ser Lys Ala Lys Gly Gln Pro Arg Glu Pro Gln Val Tyr
                485             490             495

Thr Leu Pro Pro Ser Arg Asp Glu Leu Thr Lys Asn Gln Val Ser Leu
            500             505             510

Thr Cys Leu Val Lys Gly Phe Tyr Pro Ser Asp Ile Ala Val Glu Trp
            515             520             525

Glu Ser Asn Gly Gln Pro Glu Asn Asn Tyr Lys Thr Thr Pro Pro Val
            530             535             540

Leu Asp Ser Asp Gly Ser Phe Phe Leu Tyr Ser Lys Leu Thr Val Asp
545             550             555             560

Lys Ser Arg Trp Gln Gln Gly Asn Val Phe Ser Cys Ser Val Met His
                565             570             575

Glu Ala Leu His Asn His Tyr Thr Gln Lys Ser Leu Ser Leu Ser Pro
                580             585             590

Gly Lys

<210> SEQ ID NO 38
<211> LENGTH: 337
<212> TYPE: PRT
<213> ORGANISM: Artificial Sequence
<220> FEATURE:
<223> OTHER INFORMATION: Synthetic

<400> SEQUENCE: 38

Ser Glu Thr Gln Glu Cys Leu Phe Phe Asn Ala Asn Trp Glu Lys Asp
1               5               10              15

Arg Thr Asn Gln Thr Gly Val Glu Pro Cys Tyr Gly Asp Lys Asp Lys
                20              25              30

Arg Arg His Cys Phe Ala Thr Trp Lys Asn Ile Ser Gly Ser Ile Glu
            35              40              45

Ile Val Lys Gln Gly Cys Trp Leu Asp Asp Ile Asn Cys Tyr Asp Arg
        50              55              60

Thr Asp Cys Val Glu Lys Lys Asp Ser Pro Glu Val Tyr Phe Cys Cys
65              70              75              80

Cys Glu Gly Asn Met Cys Asn Glu Lys Phe Ser Tyr Phe Pro Glu Met
                85              90              95

Glu Val Thr Gln Pro Thr Ser Asn Pro Val Thr Pro Lys Pro Asp Lys
            100             105             110

Thr His Thr Cys Pro Pro Cys Pro Ala Pro Glu Leu Leu Gly Gly Pro
            115             120             125

Ser Val Phe Leu Phe Pro Pro Lys Pro Lys Asp Thr Leu Met Ile Ser
            130             135             140

Arg Thr Pro Glu Val Thr Cys Val Val Val Asp Val Ser His Glu Asp
145             150             155             160

Pro Glu Val Lys Phe Asn Trp Tyr Val Asp Gly Val Glu Val His Asn
                165             170             175

Ala Lys Thr Lys Pro Arg Glu Glu Gln Tyr Asn Ser Thr Tyr Arg Val
                180             185             190

Val Ser Val Leu Thr Val Leu His Gln Asp Trp Leu Asn Gly Lys Glu
            195             200             205

Tyr Lys Cys Lys Val Ser Asn Lys Ala Leu Pro Ala Pro Ile Glu Lys
            210             215             220
```

-continued

```
Thr Ile Ser Lys Ala Lys Gly Gln Pro Arg Glu Pro Gln Val Tyr Thr
225             230             235             240

Leu Pro Pro Ser Arg Asp Glu Leu Thr Lys Asn Gln Val Ser Leu Thr
            245             250             255

Cys Leu Val Lys Gly Phe Tyr Pro Ser Asp Ile Ala Val Glu Trp Glu
        260             265             270

Ser Asn Gly Gln Pro Glu Asn Asn Tyr Lys Thr Thr Pro Pro Val Leu
        275             280             285

Asp Ser Asp Gly Ser Phe Phe Leu Tyr Ser Lys Leu Thr Val Asp Lys
    290             295             300

Ser Arg Trp Gln Gln Gly Asn Val Phe Ser Cys Ser Val Met His Glu
305             310             315             320

Ala Leu His Asn His Tyr Thr Gln Lys Ser Leu Ser Leu Ser Pro Gly
            325             330             335

Lys
```

```
<210> SEQ ID NO 39
<211> LENGTH: 340
<212> TYPE: PRT
<213> ORGANISM: Artificial Sequence
<220> FEATURE:
<223> OTHER INFORMATION: Synthetic
```

```
<400> SEQUENCE: 39
```

```
Glu Ala Glu Thr Arg Glu Cys Ile Tyr Tyr Asn Ala Asn Trp Glu Leu
1               5               10              15

Glu Arg Thr Asn Gln Ser Gly Leu Glu Arg Cys Glu Gly Glu Gln Asp
            20              25              30

Lys Arg Leu His Cys Tyr Ala Ser Trp Arg Asn Ser Ser Gly Thr Ile
        35              40              45

Glu Leu Val Lys Lys Gly Cys Trp Leu Asp Asp Phe Asn Cys Tyr Asp
    50              55              60

Arg Gln Glu Cys Val Ala Thr Glu Glu Asn Pro Gln Val Tyr Phe Cys
65              70              75              80

Cys Cys Glu Gly Asn Phe Cys Asn Glu Arg Phe Thr His Leu Pro Glu
            85              90              95

Ala Gly Gly Pro Glu Val Thr Tyr Glu Pro Pro Pro Thr Ala Pro Ser
        100             105             110

Gly Asp Lys Thr His Thr Cys Pro Pro Cys Pro Ala Pro Glu Leu Leu
        115             120             125

Gly Gly Pro Ser Val Phe Leu Phe Pro Pro Lys Pro Lys Asp Thr Leu
    130             135             140

Met Ile Ser Arg Thr Pro Glu Val Thr Cys Val Val Val Asp Val Ser
145             150             155             160

His Glu Asp Pro Glu Val Lys Phe Asn Trp Tyr Val Asp Gly Val Glu
            165             170             175

Val His Asn Ala Lys Thr Lys Pro Arg Glu Glu Gln Tyr Asn Ser Thr
            180             185             190

Tyr Arg Val Val Ser Val Leu Thr Val Leu His Gln Asp Trp Leu Asn
        195             200             205

Gly Lys Glu Tyr Lys Cys Lys Val Ser Asn Lys Ala Leu Pro Ala Pro
    210             215             220

Ile Glu Lys Thr Ile Ser Lys Ala Lys Gly Gln Pro Arg Glu Pro Gln
225             230             235             240
```

-continued

```
Val Tyr Thr Leu Pro Pro Ser Arg Asp Glu Leu Thr Lys Asn Gln Val
            245                 250                 255

Ser Leu Thr Cys Leu Val Lys Gly Phe Tyr Pro Ser Asp Ile Ala Val
            260                 265                 270

Glu Trp Glu Ser Asn Gly Gln Pro Glu Asn Asn Tyr Lys Thr Thr Pro
            275                 280                 285

Pro Val Leu Asp Ser Asp Gly Ser Phe Phe Leu Tyr Ser Lys Leu Thr
            290                 295                 300

Val Asp Lys Ser Arg Trp Gln Gln Gly Asn Val Phe Ser Cys Ser Val
305                 310                 315                 320

Met His Glu Ala Leu His Asn His Tyr Thr Gln Lys Ser Leu Ser Leu
                325                 330                 335

Ser Pro Gly Lys
            340
```

```
<210> SEQ ID NO 40
<211> LENGTH: 513
<212> TYPE: PRT
<213> ORGANISM: Homo sapiens
<220> FEATURE:
<221> NAME/KEY: CARBOHYD
<222> LOCATION: (241)..(241)
<223> OTHER INFORMATION: N-linked glycosylation
<220> FEATURE:
<221> NAME/KEY: CARBOHYD
<222> LOCATION: (269)..(269)
<223> OTHER INFORMATION: N-linked glycosylation
<220> FEATURE:
<221> NAME/KEY: CARBOHYD
<222> LOCATION: (386)..(386)
<223> OTHER INFORMATION: N-linked glycosylation
<220> FEATURE:
<221> NAME/KEY: CARBOHYD
<222> LOCATION: (404)..(404)
<223> OTHER INFORMATION: N-linked glycosylation
<220> FEATURE:
<221> NAME/KEY: DISULFID
<222> LOCATION: (412)..(478)
<220> FEATURE:
<221> NAME/KEY: DISULFID
<222> LOCATION: (441)..(510)
<220> FEATURE:
<221> NAME/KEY: DISULFID
<222> LOCATION: (445)..(512)
<220> FEATURE:
<221> NAME/KEY: CARBOHYD
<222> LOCATION: (454)..(454)
<223> OTHER INFORMATION: N-linked glycosylation
<220> FEATURE:
<221> NAME/KEY: DISULFID
<222> LOCATION: (477)..(477)
<220> FEATURE:
<221> NAME/KEY: DISULFID
<222> LOCATION: (477)..(477)
<223> OTHER INFORMATION: interchain

<400> SEQUENCE: 40

Met Pro Gly Leu Gly Arg Arg Ala Gln Trp Leu Cys Trp Trp Trp Gly
1               5                   10                  15

Leu Leu Cys Ser Cys Cys Gly Pro Pro Pro Leu Arg Pro Pro Leu Pro
            20                  25                  30

Ala Ala Ala Ala Ala Ala Ala Gly Gly Gln Leu Leu Gly Asp Gly Gly
            35                  40                  45

Ser Pro Gly Arg Thr Glu Gln Pro Pro Ser Pro Gln Ser Ser Ser
        50                  55                  60

Gly Phe Leu Tyr Arg Arg Leu Lys Thr Gln Glu Lys Arg Glu Met Gln
65                  70                  75                  80
```

```
Lys Glu Ile Leu Ser Val Leu Gly Leu Pro His Arg Pro Arg Pro Leu
            85              90              95

His Gly Leu Gln Gln Pro Gln Pro Pro Ala Leu Arg Gln Gln Glu Glu
            100             105             110

Gln Gln Gln Gln Gln Gln Leu Pro Arg Gly Glu Pro Pro Pro Gly Arg
            115             120             125

Leu Lys Ser Ala Pro Leu Phe Met Leu Asp Leu Tyr Asn Ala Leu Ser
    130             135             140

Ala Asp Asn Asp Glu Asp Gly Ala Ser Glu Gly Glu Arg Gln Gln Ser
145             150             155             160

Trp Pro His Glu Ala Ala Ser Ser Ser Gln Arg Arg Gln Pro Pro Pro
            165             170             175

Gly Ala Ala His Pro Leu Asn Arg Lys Ser Leu Leu Ala Pro Gly Ser
            180             185             190

Gly Ser Gly Gly Ala Ser Pro Leu Thr Ser Ala Gln Asp Ser Ala Phe
            195             200             205

Leu Asn Asp Ala Asp Met Val Met Ser Phe Val Asn Leu Val Glu Tyr
    210             215             220

Asp Lys Glu Phe Ser Pro Arg Gln Arg His His Lys Glu Phe Lys Phe
225             230             235             240

Asn Leu Ser Gln Ile Pro Glu Gly Glu Val Val Thr Ala Ala Glu Phe
            245             250             255

Arg Ile Tyr Lys Asp Cys Val Met Gly Ser Phe Lys Asn Gln Thr Phe
            260             265             270

Leu Ile Ser Ile Tyr Gln Val Leu Gln Glu His Gln His Arg Asp Ser
    275             280             285

Asp Leu Phe Leu Leu Asp Thr Arg Val Val Trp Ala Ser Glu Glu Gly
    290             295             300

Trp Leu Glu Phe Asp Ile Thr Ala Thr Ser Asn Leu Trp Val Val Thr
305             310             315             320

Pro Gln His Asn Met Gly Leu Gln Leu Ser Val Val Thr Arg Asp Gly
            325             330             335

Val His Val His Pro Arg Ala Ala Gly Leu Val Gly Arg Asp Gly Pro
            340             345             350

Tyr Asp Lys Gln Pro Phe Met Val Ala Phe Phe Lys Val Ser Glu Val
            355             360             365

His Val Arg Thr Thr Arg Ser Ala Ser Ser Arg Arg Arg Gln Gln Ser
    370             375             380

Arg Asn Arg Ser Thr Gln Ser Gln Asp Val Ala Arg Val Ser Ser Ala
385             390             395             400

Ser Asp Tyr Asn Ser Ser Glu Leu Lys Thr Ala Cys Arg Lys His Glu
            405             410             415

Leu Tyr Val Ser Phe Gln Asp Leu Gly Trp Gln Asp Trp Ile Ile Ala
            420             425             430

Pro Lys Gly Tyr Ala Ala Asn Tyr Cys Asp Gly Glu Cys Ser Phe Pro
            435             440             445

Leu Asn Ala His Met Asn Ala Thr Asn His Ala Ile Val Gln Thr Leu
    450             455             460

Val His Leu Met Asn Pro Glu Tyr Val Pro Lys Pro Cys Cys Ala Pro
465             470             475             480

Thr Lys Leu Asn Ala Ile Ser Val Leu Tyr Phe Asp Asp Asn Ser Asn
            485             490             495
```

```
Val Ile Leu Lys Lys Tyr Arg Asn Met Val Val Arg Ala Cys Gly Cys
            500             505             510

His
```

<210> SEQ ID NO 41
<211> LENGTH: 10
<212> TYPE: DNA
<213> ORGANISM: Homo sapiens
<220> FEATURE:
<221> NAME/KEY: misc_feature
<222> LOCATION: (1)..(10)
<223> OTHER INFORMATION: n is a, c, g, or t

<400> SEQUENCE: 41

```
nnnnnnnnnn                                                          10
```

<210> SEQ ID NO 42
<211> LENGTH: 510
<212> TYPE: PRT
<213> ORGANISM: Mus musculus
<220> FEATURE:
<221> NAME/KEY: CARBOHYD
<222> LOCATION: (238)..(238)
<223> OTHER INFORMATION: N-linked glycosylation
<220> FEATURE:
<221> NAME/KEY: CARBOHYD
<222> LOCATION: (266)..(266)
<223> OTHER INFORMATION: N-linked glycosylation
<220> FEATURE:
<221> NAME/KEY: CARBOHYD
<222> LOCATION: (383)..(383)
<223> OTHER INFORMATION: N-linked glycosylation
<220> FEATURE:
<221> NAME/KEY: CARBOHYD
<222> LOCATION: (401)..(401)
<223> OTHER INFORMATION: N-linked glycosylation
<220> FEATURE:
<221> NAME/KEY: DISULFID
<222> LOCATION: (409)..(475)
<220> FEATURE:
<221> NAME/KEY: DISULFID
<222> LOCATION: (438)..(507)
<220> FEATURE:
<221> NAME/KEY: DISULFID
<222> LOCATION: (442)..(509)
<220> FEATURE:
<221> NAME/KEY: CARBOHYD
<222> LOCATION: (451)..(451)
<223> OTHER INFORMATION: N-linked glycosylation
<220> FEATURE:
<221> NAME/KEY: DISULFID
<222> LOCATION: (474)..(474)
<223> OTHER INFORMATION: Interchain

<400> SEQUENCE: 42

```
Met Pro Gly Leu Gly Arg Arg Ala Gln Trp Leu Cys Trp Trp Trp Gly
1               5                   10                  15

Leu Leu Cys Ser Cys Gly Pro Pro Pro Leu Arg Pro Pro Leu Pro Val
            20                  25                  30

Ala Ala Ala Ala Ala Gly Gly Gln Leu Leu Gly Ala Gly Gly Ser Pro
        35                  40                  45

Val Arg Ala Glu Gln Pro Pro Pro Gln Ser Ser Ser Ser Gly Phe Leu
    50                  55                  60

Tyr Arg Arg Leu Lys Thr His Glu Lys Arg Glu Met Gln Lys Glu Ile
65                  70                  75                  80

Leu Ser Val Leu Gly Leu Pro His Arg Pro Arg Pro Leu His Gly Leu
            85                  90                  95

Gln Gln Pro Gln Pro Pro Val Leu Pro Pro Gln Gln Gln Gln Gln Gln
```

```
               100              105              110
Gln Gln Gln Gln Thr Ala Arg Glu Glu Pro Pro Gly Arg Leu Lys
        115              120              125

Ser Ala Pro Leu Phe Met Leu Asp Leu Tyr Asn Ala Leu Ser Asn Asp
    130              135              140

Asp Glu Glu Asp Gly Ala Ser Glu Gly Val Gly Gln Glu Pro Gly Ser
145              150              155              160

His Gly Gly Ala Ser Ser Ser Gln Leu Arg Gln Pro Ser Pro Gly Ala
            165              170              175

Ala His Ser Leu Asn Arg Lys Ser Leu Leu Ala Pro Gly Pro Gly Gly
            180              185              190

Gly Ala Ser Pro Leu Thr Ser Ala Gln Asp Ser Ala Phe Leu Asn Asp
            195              200              205

Ala Asp Met Val Met Ser Phe Val Asn Leu Val Glu Tyr Asp Lys Glu
    210              215              220

Phe Ser Pro His Gln Arg His His Lys Glu Phe Lys Phe Asn Leu Ser
225              230              235              240

Gln Ile Pro Glu Gly Glu Ala Val Thr Ala Ala Glu Phe Arg Val Tyr
            245              250              255

Lys Asp Cys Val Val Gly Ser Phe Lys Asn Gln Thr Phe Leu Ile Ser
            260              265              270

Ile Tyr Gln Val Leu Gln Glu His Gln His Arg Asp Ser Asp Leu Phe
    275              280              285

Leu Leu Asp Thr Arg Val Val Trp Ala Ser Glu Glu Gly Trp Leu Glu
    290              295              300

Phe Asp Ile Thr Ala Thr Ser Asn Leu Trp Val Val Thr Pro Gln His
305              310              315              320

Asn Met Gly Leu Gln Leu Ser Val Val Thr Arg Asp Gly Leu His Val
            325              330              335

Asn Pro Arg Ala Ala Gly Leu Val Gly Arg Asp Gly Pro Tyr Asp Lys
            340              345              350

Gln Pro Phe Met Val Ala Phe Phe Lys Val Ser Glu Val His Val Arg
            355              360              365

Thr Thr Arg Ser Ala Ser Ser Arg Arg Arg Gln Gln Ser Arg Asn Arg
    370              375              380

Ser Thr Gln Ser Gln Asp Val Ser Arg Gly Ser Gly Ser Ser Asp Tyr
385              390              395              400

Asn Gly Ser Glu Leu Lys Thr Ala Cys Lys Lys His Glu Leu Tyr Val
            405              410              415

Ser Phe Gln Asp Leu Gly Trp Gln Asp Trp Ile Ile Ala Pro Lys Gly
            420              425              430

Tyr Ala Ala Asn Tyr Cys Asp Gly Glu Cys Ser Phe Pro Leu Asn Ala
            435              440              445

His Met Asn Ala Thr Asn His Ala Ile Val Gln Thr Leu Val His Leu
    450              455              460

Met Asn Pro Glu Tyr Val Pro Lys Pro Cys Cys Ala Pro Thr Lys Leu
465              470              475              480

Asn Ala Ile Ser Val Leu Tyr Phe Asp Asp Asn Ser Asn Val Ile Leu
            485              490              495

Lys Lys Tyr Arg Asn Met Val Val Arg Ala Cys Gly Cys His
            500              505              510
```

<210> SEQ ID NO 43

-continued

```
<211> LENGTH: 10
<212> TYPE: DNA
<213> ORGANISM: Mus musculus
<220> FEATURE:
<221> NAME/KEY: misc_feature
<222> LOCATION: (1)..(10)
<223> OTHER INFORMATION: n is a, c, g, or t

<400> SEQUENCE: 43 nnnnnnnnnn                                                                  10
```